US012575811B2

(12) United States Patent
Chen et al.

(10) Patent No.: US 12,575,811 B2
(45) Date of Patent: ***Mar. 17, 2026

(54) DIAGNOSIS OF RESPIRATORY DISEASES BY CAPTURING AEROSOLIZED BIOMATERIAL PARTICLES USING PACKED BED SYSTEMS AND METHODS

(71) Applicant: Zeteo Tech, Inc., Sykesville, MD (US)

(72) Inventors: Dapeng Chen, Sykesville, MD (US); Wayne A. Bryden, Sykesville, MD (US); Michael McLoughlin, Sykesville, MD (US)

(73) Assignee: Zeteo Tech, Inc., Sykesville, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/284,273

(22) PCT Filed: Mar. 31, 2022

(86) PCT No.: PCT/US2022/022964
§ 371 (c)(1),
(2) Date: Sep. 26, 2023

(87) PCT Pub. No.: WO2022/212796
PCT Pub. Date: Oct. 6, 2022

(65) Prior Publication Data
US 2024/0148274 A1 May 9, 2024

Related U.S. Application Data

(60) Provisional application No. 63/325,435, filed on Mar. 30, 2022, provisional application No. 63/249,357, (Continued)

(51) Int. Cl.
*A61B 10/00* (2006.01)
*A61B 5/00* (2006.01)
(Continued)

(52) U.S. Cl.
CPC ............ *A61B 10/00* (2013.01); *A61B 5/0836* (2013.01); *A61B 5/097* (2013.01); *A61B 5/7203* (2013.01);
(Continued)

(58) Field of Classification Search
CPC ....... A61B 5/08; A61B 5/0836; A61B 5/7203; A61B 5/082; A61B 5/087
(Continued)

(56) References Cited

U.S. PATENT DOCUMENTS 6,062,392 A 5/2000 Birmingham et al.
6,267,016 B1 7/2001 Call et al.
(Continued)

FOREIGN PATENT DOCUMENTS

EP 3336543 A1 6/2018
EP 2823300 B1 10/2019
(Continued)

OTHER PUBLICATIONS

International Preliminary Report on Patentability (with Annex) for PCT/US2022/022964, dated May 11, 2023 by IPEA/KR.
(Continued)

*Primary Examiner* — Puya Agahi
(74) *Attorney, Agent, or Firm* — Paradice & Li LLP; Anand S. Chellappa

(57) ABSTRACT

Methods and devices for capturing and analyzing aerosolized particles in exhaled breath characteristic of a respiratory disease to enable rapid, low-cost point of care assays for several diseases including respiratory tract diseases such as COVID-19 are disclosed. The disclosed methods and systems selectively capture aerosolized particles using a packed bed column. The captured particles are then eluted using solvents and analyzed using analytical devices including MALDI-TOFMS.

15 Claims, 15 Drawing Sheets

Figure 1:
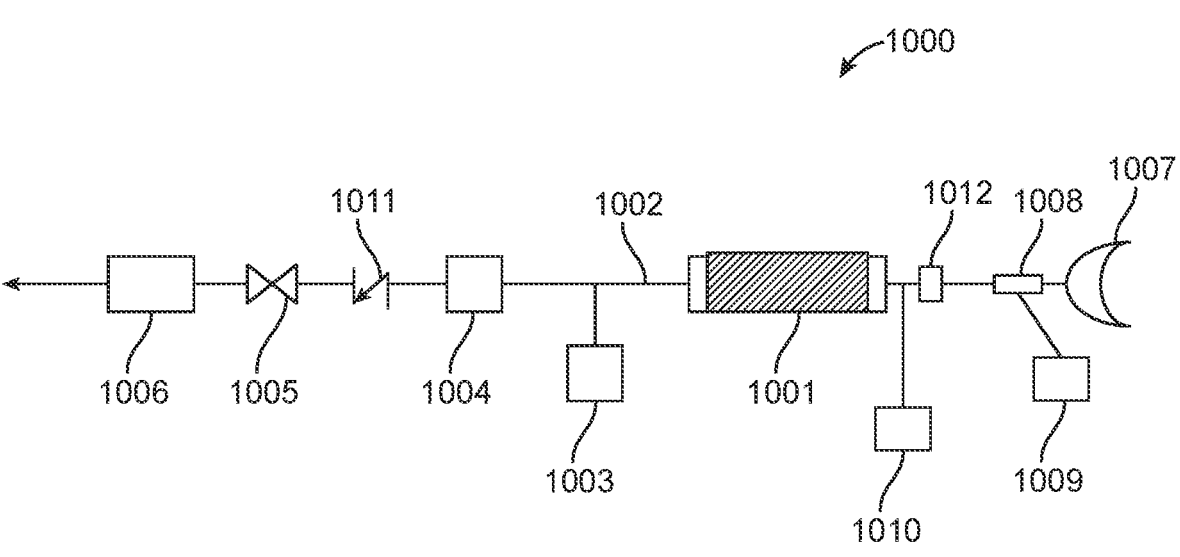

Related U.S. Application Data filed on Sep. 28, 2021, provisional application No. 63/169,130, filed on Mar. 31, 2021.

(51) Int. Cl.

| | |
|---|---|
| *A61B 5/083* | (2006.01) |
| *A61B 5/097* | (2006.01) |
| *A61M 16/04* | (2006.01) |
| *A61M 16/08* | (2006.01) |
| *G01N 1/40* | (2006.01) |
| *G01N 33/68* | (2006.01) |

(52) U.S. Cl.
CPC ...... *A61M 16/0808* (2013.01); *A61M 16/085* (2014.02); *G01N 1/4044* (2013.01); *G01N 33/6848* (2013.01); *G01N 33/6851* (2013.01); *G01N 33/6893* (2013.01); *A61B 2010/0087* (2013.01); *A61B 2560/0431* (2013.01); *A61M 16/04* (2013.01); *G01N 2800/12* (2013.01); *G01N 2800/26* (2013.01)

(58) Field of Classification Search
USPC ........................................................ 600/532
See application file for complete search history.

(56) References Cited

U.S. PATENT DOCUMENTS

| | | | |
|---|---|---|---|
| 6,534,769 B1 * | 3/2003 | Graham ............... A61B 5/0836 |
| | | | 250/343 |
| 7,779,840 B2 | 8/2010 | Acker et al. | |
| 8,409,870 B2 | 4/2013 | Van Wuijckhuijse et al. | |
| 8,424,523 B2 | 4/2013 | Ogilvie et al. | |
| 8,434,481 B2 | 5/2013 | Ogilvie et al. | |
| 8,434,483 B2 | 5/2013 | Patel et al. | |
| 8,944,059 B2 | 2/2015 | Mansour et al. | |
| 9,022,029 B2 | 5/2015 | Varga et al. | |
| 9,089,665 B2 | 7/2015 | Patel | |
| 9,675,773 B2 | 6/2017 | Colman et al. | |
| 10,632,276 B2 | 4/2020 | Fyfe et al. | |
| 10,926,052 B2 | 2/2021 | Colman et al. | |
| 11,135,392 B2 | 10/2021 | Oddo et al. | |
| 11,229,763 B2 | 1/2022 | Oddo et al. | |
| 11,246,506 B2 | 2/2022 | Gunneson et al. | |
| 11,359,733 B2 | 6/2022 | Oddo et al. | |
| 11,400,250 B2 | 8/2022 | Oddo et al. | |
| 11,547,322 B2 | 1/2023 | Lundin et al. | |
| 11,617,848 B2 | 4/2023 | Fyfe et al. | |
| 11,658,021 B2 | 5/2023 | Bryden et al. | |
| 11,826,512 B2 | 11/2023 | Oddo et al. | |
| 11,896,366 B2 | 2/2024 | Cardin | |
| 11,996,280 B2 | 5/2024 | McLoughlin | |
| 12,091,056 B2 | 9/2024 | Ramakrishnan et al. | |
| 2003/0208132 A1 | 11/2003 | Baddour | |
| 2005/0137491 A1 | 6/2005 | Paz et al. | |
| 2007/0068811 A1 | 3/2007 | Tsukashima et al. | |
| 2008/0038207 A1 | 2/2008 | Edwards et al. | |
| 2009/0156952 A1 | 6/2009 | Hunter et al. | |
| 2010/0252046 A1 * | 10/2010 | Dahlstrom .......... A61M 16/205 |
| | | | 128/205.24 |
| 2012/0011918 A1 | 1/2012 | Bacal et al. | |
| 2012/0172679 A1 | 7/2012 | Logan et al. | |
| 2013/0217029 A1 | 8/2013 | Sislian et al. | |
| 2013/0327122 A1 | 12/2013 | Dutta et al. | |
| 2015/0377868 A1 | 12/2015 | Cooper et al. | |
| 2016/0020080 A1 | 1/2016 | Pyun et al. | |
| 2016/0022946 A1 | 1/2016 | Sislian et al. | |
| 2016/0231333 A1 | 8/2016 | Sutherland | |
| 2017/0035326 A1 | 2/2017 | King-Smith | |
| 2017/0119280 A1 | 5/2017 | Ahmad | |
| 2017/0299477 A1 | 10/2017 | Milton et al. | |
| 2017/0303822 A1 | 10/2017 | Allsworth et al. | |
| 2018/0246120 A1 | 8/2018 | Bryden et al. | |
| 2019/0000351 A1 | 1/2019 | Scampoli | |

| | | | |
|---|---|---|---|
| 2019/0094195 A1 | 3/2019 | Genter | |
| 2019/0282124 A1 | 9/2019 | Wu et al. | |
| 2020/0041485 A1 | 2/2020 | Funch-Nielsen | |
| 2020/0147333 A1 * | 5/2020 | Stoll ................. A61M 16/0858 |
| 2020/0321793 A1 * | 10/2020 | Al-Ali ................. A61B 5/0006 |
| 2020/0345266 A1 | 11/2020 | Schleich | |
| 2021/0318208 A1 | 10/2021 | Bayer et al. | |
| 2021/0321903 A1 | 10/2021 | Daniels | |
| 2021/0345956 A1 | 11/2021 | Keays et al. | |
| 2021/0386959 A1 | 12/2021 | Oddo et al. | |
| 2022/0034854 A1 * | 2/2022 | Chen ..................... A61B 5/091 |
| 2022/0076783 A1 | 3/2022 | Cristescu et al. | |
| 2022/0183587 A1 | 6/2022 | Karshmer | |
| 2022/0323045 A1 | 10/2022 | Chen et al. | |
| 2022/0370751 A1 | 11/2022 | Oddo et al. | |
| 2022/0381766 A1 | 12/2022 | Cardin | |
| 2023/0157573 A1 | 5/2023 | Chen et al. | |
| 2023/0172484 A1 | 6/2023 | Lundin et al. | |
| 2023/0256189 A1 | 8/2023 | Fyfe et al. | |
| 2024/0197202 A1 | 6/2024 | Andrasko et al. | |
| 2024/0423497 A1 | 12/2024 | Höjer | |

FOREIGN PATENT DOCUMENTS

| | | |
|---|---|---|
| JP | H0989863 A | 4/1997 |
| JP | H09126958 A | 5/1997 |
| JP | H10227725 A | 8/1998 |
| JP | 2006329779 A | 12/2006 |
| JP | 2011102747 A | 5/2011 |
| JP | 5848608 B2 | 1/2016 |
| JP | 2018194463 A | 12/2018 |
| JP | 2019184288 A | 10/2019 |
| JP | 2020534511 A | 11/2020 |
| KR | 1020160130229 | 11/2016 |
| WO | WO2004090534 A1 | 10/2004 |
| WO | WO2006012205 A2 | 2/2006 |
| WO | WO2009045163 A1 | 4/2009 |
| WO | WO2017197386 A1 | 11/2017 |
| WO | WO2019011750 A1 | 1/2019 |
| WO | WO2019145678 A1 | 8/2019 |
| WO | WO2021041571 A1 | 3/2021 |
| WO | WO2021061330 A1 | 4/2021 |
| WO | WO2021201905 A1 | 10/2021 |

OTHER PUBLICATIONS

International Search Report and Written Opinion for PCT/US2020/048035, issued by ISA/KIPO on Dec. 30, 2020.

Written Opinion of ISA/KIPO for PCT/US2020/048040 issued Dec. 9, 2020.

International Preliminary Report on Patentability (with Annex) for PCT/US2020/048035, mailed Mar. 22, 2022 by IPEA/KR.

International Search Report and Written Opinion of ISA/KIPO for PCT/US2022/022964 issued Jul. 13, 2022.

Hunt, J., "Exhaled breath condensate: An evolving tool for noninvasive evaluation of lung disease," J. Allergy Clin. Immunol. 2002; 110:28-34.

Benjamin Patterson, Carl Morrow, Vinayak Singh, Atica Moosa, Melitta Gqada, Jeremy Woodward, Valerie Mizrahi, Wayne Bryden, Charles Call, Shwetak Patel, Digby Warner, Robin Wood, "Detection of *Mycobacterium tuberculosis* bacilli in bio-aerosols from untreated TB patients," Gates Open Research 2018, 1:11.

B. Bake, P. Larsson, G. Ljungkvist, E. Ljungström, and A-C Olin, "Exhaled particles and small airways," Respiratory Research (2019) 20:8.

Fennelly K.P., Martyny J.W., Fulton K.E., Orme I.M., Cave D.M., et al. (2004) Cough-generated aerosols of *Mycobacterium tuberculosis*: a new method to study infectiousness. Am J Respir Crit Care Med 169: 604-609.

Dina Hashoul and Hossam Haick, "Sensors for detecting pulmonary diseases from exhaled breath," Eur. Respir. Rev. 2019; 28: 190011.

Maria D. King, Andrew R. McFarland, "Bioaerosol Sampling with a Wetted Wall Cyclone: Cell Culturability and DNA Integrity of *Escherichia coli* Bacteria," Aerosol Sci. Technol., 46:82-93, 2012.

James J. McDevitt, Petros Koutrakis, Stephen T. Ferguson, Jack M. Wolfson, M. Patricia Fabian, Marco Martins, Jovan Pantelic, and

(56)            References Cited

OTHER PUBLICATIONS

Donald K. Milton, "Development and Performance Evaluation of an Exhaled-Breath Bioaerosol Collector for Influenza Virus," Aerosol Sci. Technol. Jan. 1, 2013; 47(4): 444-451.

Wood R., Morrow C., Barry C.E., III, Bryden W.A., Call C.J., Hickey A.J., et al.: Real-Time Investigation of Tuberculosis Transmission: Developing the Respiratory Aerosol Sampling Chamber (Rasc). PLoS One. 2016; 11(1): e0146658.

Rachel C. Wood, Angelique K. Luabeya, Kris M. Weigel, Alicia K. Wilbur, Lisa Jones-Engel, Mark Hatherill, and Gerard A. Cangelosi, "Detection of *Mycobacterium tuberculosis* DNA on the oral mucosa of tuberculosis patients," Sci. Rep. 5, 8668 (2015).

Fatima B. Wurie, Stephen D. Lawn, Helen Booth, Pam Sonnenberg, Andrew C. Hayward, "Bioaerosol production by patients with tuberculosis during normal tidal breathing: implications for transmission risk," Thorax 2016; 71: 549-554.

International Search Report and Written Opinion of ISA/KIPO for PCT/US2023/029760 dated Nov. 24, 2023.

"Ventilator/Ventilator Support, What to Expect," NIH, National Heart, Lung, and Blood Institute, downloaded from the Internet on Jul. 8, 2024 at <https://www.nhlbi.nih.gov/health/ventilator/what-to-expect#:~:text=Ventilators>, 7-pages, last updated Mar. 24, 2022.

Chen et al., "A Novel System for the Comprehensive Collection of Nonvolatile Molecules from Human Exhaled Breath," Journal of Breath Research, vol. 15, No. 1, Oct. 20, 2020 (Oct. 20, 2020), p. 016001, XP09328706.

Chen et al., 'Noninvasive Proteomic Markers for Respiratory Tract Infections in Mechanically Ventilated Patients', medRxiv, Aug. 18, 2022, [retrieved on Jan. 18, 2025]. Retrieved from <URL: https://www.medrxiv.org/content/10.1101/2022.08.17.22278888v1>, pp. 3, 7, and figure 1.

International Search Report and Written Opinion of ISA/KIPO for PCT/US2024/052658 dated Feb. 6, 2025.

Khamchun et al., 'Coronin-1A serves as a serum biomarker for supportive diagnosis of Mycobacterium tuberculosis infection', Germs, Mar. 2023, pp. 20-31, [retrieved on Jan. 18, 2025]. Retrieved from <URL: https://pmc.ncbi.nlm.nih.gov/articles/PMC10659747>, p. 22 and table 1.

Song et al., 'Proteomic Profiling of Serum from Patients with Tuberculosis', Ann Lab Med 2014, 34(5), pp. 345-353, [retrieved on Jan. 18, 2025]. Retrieved from <URL: https://doi.org/10.3343/alm.2014.34.5.345>, p. 347 and table 1.

International Preliminary Report on Patentability (with Annex) for PCT/US2023/029760 dated Oct. 8, 2024 by IPEA/KR.

Guise M T et al: ""An experimental investigation of aerosol collection utilizing packed beds of silica aerogel microspheres"", Journal of Non-Crystalline Solids, North-Holland Physics Publishing. Amsterdam, NL, vol. 285, No. 1-3, Jun. 1, 2001 (Jun. 1, 2001), pp. 317-322, XP004242941, ISSN: 0022-3093, DOI: 10.1016/S0022-3093(01)00473-2. (Year: 2001).

Bardet, C. et al. (Jan. 23, 2021) Early and specific targeted mass spectrometry-based identification of bacteria in endotracheal aspirates of patients suspected with ventilator-associated pneumonia. European Journal of Clinical Microbiology & Infectious diseases. vol. 40, p. 1291-1301. (Year: 2021).

Lopez-Sanchez, L. et al. (2017) Exhaled breath condensate biomarkers for the early diagnosis of lung cancer using proteomics. American Journal of Physiological Lung Cell Molecular Physiology, vol. 313, L664-L676. (Year: 2017).

MaxiQuant technical note (2010): MultiQuant Software 2.0 for targeted protein/ peptide quantification, # 0921210-02. (Year: 2010).

Qu, J. et al. (2010) Proteomic expression profiling of Haemophilus influenzae grown in pooled human sputum from adults with chronic obstructive pulmonary disease reveal antioxidant and stress response. BMC Microbiology, vol. 10: 162, 12 pages. (Year: 2010).

Dupree (2020) A critical review of Bottom-up proteomics: the good, the bad and the future of this field. Proteomes, vol. 8 No. 14, 8030114, 26 pages. (Year: 2020).

Amann, A et al. (2014) Analysis of exhaled breath for disease detection. Ann Rev Anal Chem. Vol 7:435-482. (Year: 2014).

Bregy (2018) Real-time mass spectrometric identification of metabolites characteristic of chronic obstructive pulmonary disease in exhaled breath. Clinical Mass Spectrometry, vol. 7, 29-35. (Year: 2018).

Ross, M.H, et al (2019) Host-based diagnostics for acute respiratory infections. Clinical Therapeutics, vol. 41, No. 10, p. 1923-1938. (Year: 2019).

"Hsueh, M-F. (2016) Elucidating the molecular composition of cartilage by proteomics. Journal of Proteome Research, vol. 15, p374-388. (Year: 2016)".

Stegemann, C. (2013) Proteomic identification of matrix metalloproteinase substrates in the human vasculature. Circ Cardiovasc Genet. vol. 6, p. 106-117 (Year: 2013).

* cited by examiner

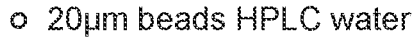
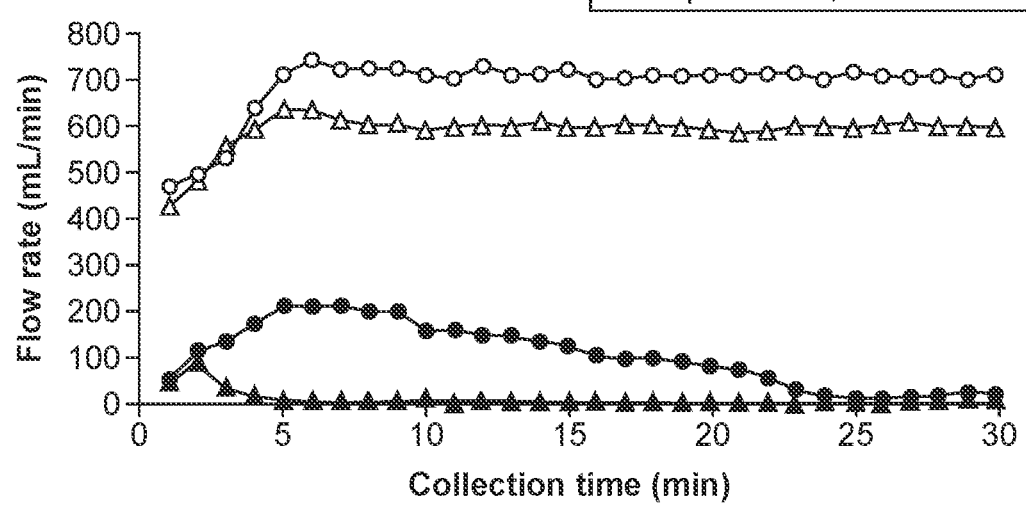
FIG. 8A
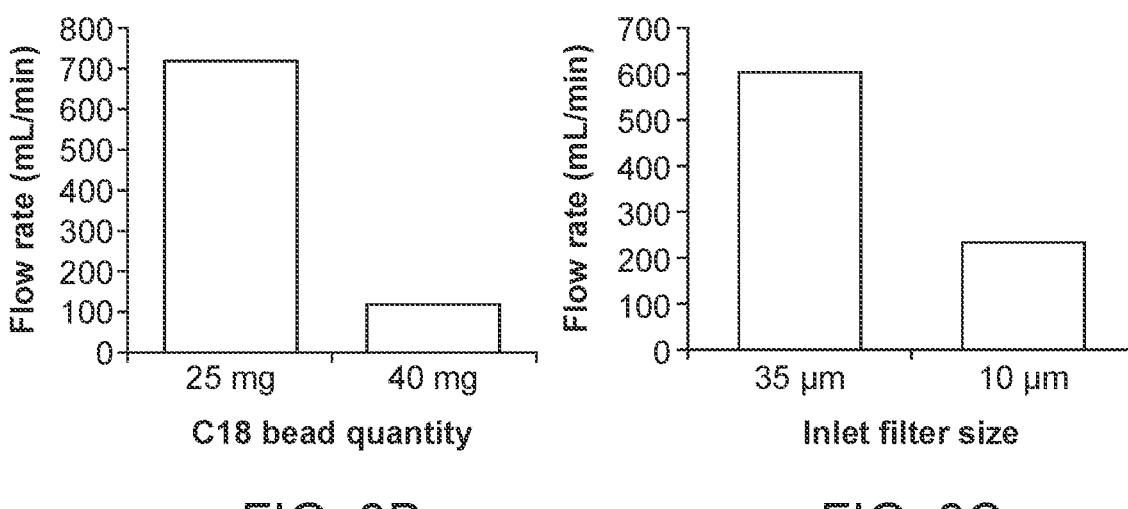
FIG. 8B                         FIG. 8C

| Allowed Missed Cleavage | Organism Identification | Protein | Score | Expect | Matches |
|---|---|---|---|---|---|
| 0 | Nucleoprotein OS=Severe acute respiratory syndrome coronavirus 2 OX=2697049 GN=N PE=1 SV=1 | NCAP_SARS2 | 59 | 0.78 | 6 |
| 1 | | | 126 | 1.40E-07 | 15 |
| 2 | | | 211 | 4.50E-16 | 24 |
| 3 | | | 250 | 5.70E-20 | 28 |
| 4 | | | 230 | 5.70E-18 | 28 |
| 5 | | | 236 | 1.40E-18 | 29 |
| 6 | | | 232 | 3.60E-18 | 29 |
| 7 | | | 231 | 4.50E-18 | 29 |
| 8 | | | 230 | 5.70E-18 | 29 |
| 9 | | | 230 | 5.70E-18 | 29 |

FIG. 15E

DIAGNOSIS OF RESPIRATORY DISEASES BY CAPTURING AEROSOLIZED BIOMATERIAL PARTICLES USING PACKED BED SYSTEMS AND METHODS

RELATED APPLICATIONS

This application is a U.S. National Stage Application of International Appl. No. PCT/US2022/022964, filed Mar. 31, 2022, which is related to and claims the benefit of U.S. Provisional Appl. No. 63/169,130, filed Mar. 31, 2021, and titled "Diagnosis of Respiratory Diseases By Capturing Aerosolized Biomaterial Particles Using Packed Bed Systems and Methods," U.S. Provisional Appl. No. 63/249,357, filed Sep. 28, 2021 and titled "Diagnosis of Respiratory Diseases By Capturing Aerosolized Biomaterial Particles Using Packed Bed Systems and Methods," and U.S. Provisional Appl. No. 63/325,435, filed Mar. 30, 2022, and titled "Diagnosis of Respiratory Diseases By Capturing Aerosolized Biomaterial Particles Using Packed Bed Systems and Methods," the entire disclosures of which are hereby incorporated herein by reference in their entireties.

FEDERALLY SPONSORED RESEARCH AND DEVELOPMENT

None.

FIELD

This disclosure relates to methods and devices for capturing and analyzing aerosolized organic biomaterials such as virus and bacteria particles in exhaled breath and other aerosols to enable rapid, low-cost point of care assays for several diseases including respiratory tract diseases such as COVID-19. More particularly, but not by way of limitation, the present disclosure relates to methods and devices for analyzing non-volatile organics in exhaled breath and other aerosols to detect respiratory diseases such as COVID-19 and tuberculosis using mass spectromtery, including MALDI-TOFMS.

BACKGROUND

Coronavirus Disease (COVID-19) is a disease caused by the newly emerged coronavirus SARS-CoV-2. This new coronavirus is a respiratory virus and spreads primarily through droplets generated when an infected person coughs or sneezes, or through droplets of saliva or discharge from the nose. The novel coronavirus is highly contagious and has created an ongoing COVID-19 pandemic which suggests that this virus is spreading more rapidly than influenza. To help in mitigation, rapid detection tools are needed.

Further, tuberculosis (TB) has surpassed HIV/AIDS as a global killer with more than 4000 daily deaths. (Patterson, B., et al., 2018). The rate of decline in incidence remains inadequate at a reported 1.5% per annum and it is unlikely that treatment alone will significantly reduce the burden of disease. In communities with highly prevalent HIV, *Mycobacterium tuberculosis* (Mtb) genotyping studies have found that recent transmission, rather than reactivation, accounts for the majority (54%) of incident TB cases. The physical process of TB transmission remains poorly understood and the application of new technologies to elucidate key events in infectious aerosol production, release, and inhalation, has been slow. Empirical studies to characterize airborne infectious particles have been sparse. Two major difficulties plaguing investigation are the purportedly low concentrations of naturally produced Mtb particles, and the complication of environmental and patient derived bacterial and fungal contamination of airborne samples. There have nonetheless been a number of attempts at airborne detection. A 2004 proof of concept study and subsequent feasibility study in Uganda sampled cough-generated aerosols from pulmonary TB patients. Coughing directly into a sampling chamber equipped with two viable cascade impactors resulted in positive cultures from more than a quarter of participants despite their having received 1-6 days of chemotherapy. A follow-up work employing the same apparatus found that participants with higher aerosol bacillary loads could be linked to greater household transmission rates and development of disease findings which suggest that quantitative airborne sampling may serve as a clinically relevant measure of infectivity. Therefore, interruption of transmission would likely have a rapid, measurable impact on TB incidence.

The best method to control transmission of tuberculosis is to promptly identify and treat active TB cases. (Wood, R. C., et al., 2015). Diagnosis of pulmonary TB is usually done by microbiological, microscopic, or molecular analysis of patient sputum. The "gold standard" test for TB infection in most of the developing world is a smear culture based on a sputum sample. The sample is smeared onto a culture plate, a stain is added that is specific to Mtb, and the stained cells are counted using a microscope. If the concentration of cells in the smear is greater than a set threshold, then the sample is classified as positive. If the TB counts are below this threshold, it is classified as negative. Diagnosis may take several hours. The need for sputum as a diagnostic sample is a limiting factor due to the challenges of collecting it from patients and to its complex composition. The viscosity of the material restricts test sensitivity, increases sample-to-sample heterogeneity, and increases costs and labor associated with testing. Moreover, sputum production (which requires coughing) is an occupational hazard for healthcare workers. Sputum has several drawbacks as a sample medium. First, only about 50% of patients can provide a good sputum sample. For example, children under about age of eight often are not able to produce a sample upon request, usually because they have not developed an ability to "cough up" sputum from deep in their throat. The elderly and ill may not have the strength to cough up sputum. Others simply may not have sputum in their throat. Thus, a diagnostic method based on sputum analysis may not provide a diagnosis in as many as 50% of the patients who are in need of diagnosis. Sputum is also not useful as a diagnostic sample if it is collected one to two days after a person has been treated with antibiotics because the sample is no longer representative of the disease state deep in the lungs, and within several days after treatment begins, the number of live Mtb in the sputum is significantly reduced. Urine and blood have been proposed as sample media for the diagnosis of TB infection. Blood is highly invasive and entails the higher cost of handling blood samples that are often HIV positive since, in some parts of the world, many TB patents also have HIV co-infections. Further, a patient with an active TB infection may not have many TB cells circulating in their blood. Urine-based diagnostics have also been proposed, but these tests look for biomarkers of the disease other than living TB bacilli, and none not been validated for widespread clinical use.

A sample that is easier, safer, and more uniform to collect and handle would simplify TB diagnosis. Exhaled breath contains aerosols ("EBA") and vapors that can be collected noninvasively and analyzed for characteristics to elucidate physiologic and pathologic processes in the lung. (Hunt, 2002). To capture the breath for assay, exhaled air is passed through a condensing apparatus to produce an accumulation of fluid that is referred to as exhaled breath condensate ("EBC"). Although predominantly derived from water vapor, EBC has dissolved within its nonvolatile compounds, including cytokines, lipids, surfactant, ions, oxidation products, and adenosine, histamine, acetylcholine, and serotonin. In addition, EBC traps potentially volatile water-soluble compounds, including ammonia, hydrogen peroxide, and ethanol, and other volatile organic compounds. EBC has readily measurable pH. EBC contains aerosolized airway lining fluid and volatile compounds that provide noninvasive indications of ongoing biochemical and inflammatory activities in the lung. Rapid increase in interest in EBC has resulted from the recognition that in lung disease, EBC has measurable characteristics that can be used to differentiate between infected and healthy individuals. These assays have provided evidence of airway and lung redox deviation, acid-base status, and degree and type of inflammation in acute and chronic asthma, chronic obstructive pulmonary disease, adult respiratory distress syndrome, occupational diseases, and cystic fibrosis. Characterized by uncertain and variable degrees of dilution, EBC may not provide precise assessment of individual solute concentrations within native airway lining fluid. However, it can provide useful information when concentrations differ substantially between health and disease or are based on ratios of solutes found in the sample.

Patterson et al. (2018) used a custom-built respiratory aerosol sampling chamber (RASC), a novel apparatus designed to optimize patient-derived exhaled breath aerosol sampling, and to isolate and accumulate respirable aerosol from a single patient. Environmental sampling detects the Mtb present after a period of ageing in the chamber air. 35 newly diagnosed, GeneXpert (Cepheid, Inc., Sunnyvale, CA) sputum-positive, TB patients were monitored during one-hour confinement in the RASC chamber which has a volume of about 1.4 m$^3$. The GeneXpert genetic assay is based on polymerase chain reaction (PCR) and may be used to analyze a sample for TB diagnosis and to indicate whether or not there are drug resistance genes in the TB sample. The GeneXpert PCR assay for TB can accept a sputum sample and provide a positive or negative result in about one hour. The chamber incorporated aerodynamic particle size detection, viable and non-viable sampling devices, real-time $CO_2$ monitoring, and cough sound-recording. Microbiological culture and droplet digital polymerase chain reaction (ddPCR) were used to detect Mtb in each of the bio-aerosol collection devices. Mtb was detected in 77% of aerosol samples and 42% of samples were positive by mycobacterial culture and 92% were positive by ddPCR. A correlation was found between cough rate and culturable bioaerosol. Mtb was detected on all viable cascade impactor stages with a peak at aerosol sizes 2.0-3.5 m. This suggests a median of 0.09 CFU/litre of exhaled air for the aerosol culture positives and an estimated median concentration of $4.5 \times 10^7$ CFU/ml of exhaled particulate bio-aerosol. Mtb was detected in bioaerosols exhaled by a majority of the untreated TB-patients using the RASC chamber. Molecular detection was found to be more sensitive that Mtb culture on solid media.

Mtb can be identified in EBA by culture, ddPCR, electron microscopy, immunoassay, and cell staining (e.g., oramine and dmn-Tre). Of these, PCR and immunoassays have the potential to be rapid and specific to the species level. PCR and other genomics-based techniques can be specific to the strain level. Mass spectrometry has also been shown to be specific to the strain level for cultures obtained from bacterial infections. For example, the Biotyper from Bruker Daltonics (Germany), has been shown to be able to identify up to 15,000 strains of bacteria that cause infections in humans. These techniques have been shown to be capable of identifying TB infection from EBA. Immunoassays for Mtb detection, such as the one based on lipoarabinomannan, are also well known.

In the case of TB, people infected with TB are often diagnosed through passive case finding when individuals present themselves to clinics. Active case finding ("ACF") is generally considered to include other methods of reaching people suspected of TB infection outside of the primary health care system. According to WHO, ACF is "systematic identification of people with suspected active TB, using tests, examinations, or other procedures that can applied rapidly." The goal of ACF is to get those infected to treatment earlier, reducing the average period of infection, and thereby reducing the spread of the disease. In the case of TB, by the time an individual goes to a clinic for help, that person may have transmitted the TB infection to between about 10 other people and about 115 other people. ACF can help to reduce or prevent significant TB transmission. The diagnostic systems and methods such as sputum analysis and blood analysis are either not automated and autonomously operated, or not rapid. Many have expensive assays that are consumed for each analysis, and thus, do not have general utility for active case finding, particularly in developing and under-developed countries. As previously described, EBA analysis appears to be a compelling diagnostic tool for TB detection that provides for rapid analysis, portability, and low cost because the need for expensive assays and consumables are eliminated. McDevitt et al. (2013) have report EBA analytical devices and methods for influenza diagnosis. An impactor is used to remove large particles (>4 μm) from exhaled breath, followed by a wetted-film collector for the smaller particles (<4 μm). The two size bins of collected particles were analyzed for influenza virus using a genomics-based method, reverse transcriptase polymerase chain reaction (rt-PCR). PCR technology uses biomolecular probes, combined with other biomolecules including enzymes, to amplify a specific sequence of DNA if that particular sequence is present in the sample. The targeted sequences are believed to be specific to the disease being identified. McDevitt et al. showed that EBA samples can be used to diagnose influenza. The disclosed devices and methods have several shortcomings from a practical standpoint. First, the breath aerosol sample is collected into discrete samples that are several milliliters in volume, and thus, considerable effort is needed to concentrate the sample. Further, the diagnostic device is not coupled to or integrated with the sample collector and is not amenable for use as an ACF tool. The ability to automate the RNA assays to create an autonomous diagnostic tool for TB analysis is not clear. A method to determine whether sufficient volume of cough or breath aerosol was generated by a particular patient is not described. As a result, if a sample is found to be negative for influenza it may be due to a false negative resulting from inadequate sample collection. It is well known that there are large variabilities among humans with respect to the volume of aerosolized lung fluid produced during various breathing maneuvers.

The GeneXpert Ultra is a state-of-the-art genomics-based point of care diagnostic device which uses PCR technology. It may be integrated with an EBA sample collection method to perform ACF of TB and other respiratory diseases, but the sample collection times would be too long to be practical. Patterson et al. have shown that between 20 and 200 TB bacilli are typically produced in EBA and can be collected over a one-hour sampling period. A minimum of one hour of sampling would be required to use the GeneXpert Ultra as a diagnostic assay. The GeneXpert may be integrated with a system that samples air to analyze air samples for airborne pathogens. The BDS system (Northup Grumman, Edgewood, MD), is being used for screening US Postal Service mail for bacterial spores that cause anthrax as the mail passes through distribution centers. It combines a wetted-wall cyclone with a GeneXpert PCR system to autonomously sample air and report if pathogens are present. However, the GeneXpert Ultra assay has a relatively high cost per test and takes approximately an hour to complete the assay and provide a result. In general, PCR-based diagnostics are unsuitable for TB screening for ACF applications due to both the extended time needed for sampling and analysis, and the relatively high cost per test.

The time associated with a diagnostic assay is a critical parameter for a fielded, or "point of care" test. ACF is an example of a fielded diagnostic assay because, by definition, ACF takes place outside the healthcare system. In the U.S., a point-of-care test needs to provide an answer in 20 minutes or less. If not, the test is considered to be too slow and not acceptable for achieving short patient wait-times. In the developing world, and especially in countries with a history of TB prevalence, the GeneXpert may be used to provide diagnosis in about one hour. As previously described, this assay is expensive to implement on a "cost per test" basis, and therefore it is not yet widely deployed. Because of high cost, it is not used to screen patients who appear healthy (non-symptomatic) but might have TB infection, but rather, is used to confirm a diagnosis that is strongly suspected based on other tests or factors.

Fennelly et al. (2004) described TB analysis using cough aerosol and a collection chamber that contains two Anderson cascade impactors using individuals who were known to have active patients. Individuals were asked to provide two discrete five-minute bursts of intense coughing. Culturing of impacted samples took 30-60 days, and therefore this approach is not amenable to automation. A challenging aspect of EBA as a clinical sample is the relatively small sample of volume of exhaled particulates that can be collected from breath. Further, a significant fraction of the mass collected is water. The molecules that contain diagnostic information ("biomarkers") are present in nanoliter or picogram quantities. Subsequently, the aerosol collection method must be effective in capturing a large fraction of the biomass in the exhaled breath. Exhaled breath includes air that is exhaled from the lungs through any number of maneuvers, including tidal breathing, deep breathing, coughing, and sneezing. Particular types of deep breathing maneuvers such as forced vital capacity (FVC), may be used to measure the maximum volume of lung capacity by breathing in as much as possible, and exhaling as far (or as deep) as possible to maximize the volume of exhaled breath. Forced expiratory volume (FEV) measures how much air a person can exhale during a forced breath. The amount of air exhaled may be measured during the first (FEV1), second (FEV2), and/or third seconds (FEV3) of the forced breath. Forced vital capacity (FVC) is the total amount of air exhaled during an FEV test. Forced expiratory volume and forced vital capacity are lung function tests that are measured during spirometry. Forced expiratory volume is an important measurement of lung function.

Although research has shown that respiratory diseases can be detected from breath aerosol and breath condensate, modern clinical tests for infections or diseases such as tuberculosis, influenza, pneumonia continue to utilize sputum, blood, or nasal swabs. Exhaled breath analytical tools have not been commercialized because methods and devices to efficiently collect and concentrate the trace amounts of analyte present in exhaled breath are lacking. Furthermore, there is no standard or methodology to assess how much exhaled breath is sufficient for a particular diagnosis. The disclosed exemplary devices and methods overcome these limitations by collecting exhaled breath aerosol and breath condensate at high flow rate, high efficiency, and into relatively concentrated samples. Further, size sorting of aerosol can be incorporated to increase the signal to noise ratio for specific analytes prior to collection of the analytes. The concentrated samples may then be analyzed by several methods, but preferably, using methods that are sensitive, rapid, and highly specific to the analytes of interest. More preferably, the analysis will be rapid, and near real-time. Mass spectrometry, real-time PCR, and immunoassays have the highest potential to be sensitive, specific and nearly real-time.

A need exists for sample collection methods that can be coupled with fast diagnostic tools such as mass spectrometry ("MS") that is more rapid and reliable than sputum analysis and less invasive than blood analysis to provide a diagnostic assay that is fast, sensitive, specific and preferably, characterized by low cost per test. Such a system could be used for active case finding (ACF) of TB and other lung or respiratory tract diseases. To be effective, a system for ACF must be rapid and inexpensive on a "per diagnosis" basis. Low cost-per-test is a requirement for screening a large number of individuals to proactively prevent TB transmission to search for the few that are indeed infected TB. Low-cost devices and methods would also be required for point-of-care diagnosis of influenza and other pathogenic viruses because patients probably infected with a "common cold" may be infected with rhinovirus. In some cases, the respiratory infection will be driven by a bacterial or fungal microbe and may be treatable with antibiotics. In other cases, the microbe may be resistant to antibiotics, and a diagnostic method that can identify microbial resistance to antibiotics is preferable. Rapid EBA methods for distinguishing between viral and bacterial infections in the respiratory tract are desired while minimizing the occurrence of false negatives due to an insufficient sample volume. Mass spectrometry, genomics methods including PCR, and immunoassays have the highest potential to be sensitive and specific. Mass spectrometry, and in particular, MALDI time-of-flight mass spectrometry (MALDI-TOFMS), is a preferred diagnostic tool for analysis EBA and EBC samples because it has been demonstrated to be sensitive, specific and near real-time.

BRIEF DISCLOSURE

Disclosed is an exemplary exhaled breath collection system for monitoring a patient infected with a respiratory disease and connected to a ventilator to assist the breathing of the infected patient, the system comprising one or more sample capture elements comprising a packed bed column in each to selectively capture aerosolized particles in the exhaled breath produced by the patient wherein the sample capture element is removably connected to the exhaled air tubing of the ventilator and, a subsystem comprising at least one of a pump, a power supply, and a controller wherein the subsystem is disposed in fluid communication with the sample capture element and is configured to control the operation of the sample capture element and wherein the pump is configured to draw the exhaled air aerosol into the sample capture element. The subsystem may further comprise at least one of a $CO_2$ sensor and a particle counter disposed between the sample capture element and the pump. The subsystem may be disposed in a portable enclosure. The system may further comprise a trap disposed between the sample capture element and the pump and configured to trap exhaled breath condensate (EBC) comprising at least one of water vapor, volatile organic components and non-volatile organic components that pass through the packed bed. The packed bed column may comprise solid particles comprising at least one of resins, cellulose, silica, agarose, and hydrated Fe3O4 nanoparticles. The packed bed column may comprise at least one of resin beads having C18 functional groups on the surface, cellulose beads having sulfate ester functional groups on the surface and mixtures thereof. The resin beads and cellulose beads may have a nominal diameter of at least about 20 μm. The resin beads and cellulose beads may have a nominal diameter of between about 40 microns and about 150 microns. The beads may be packed between two porous polymeric frit discs. The the nominal flow rate drawn through the bed using the pump may be between about 200 ml/min and about 3 L/min.

Disclosed is an exemplary for monitoring a patient infected with a respiratory disease comprising, an exemplary exhaled breath collection system as previously described, a sample extraction system to extract the captured aerosol particles characteristic of the respiratory disease from the packed bed column into one or more liquid samples, and an analytical device to analyze the aerosol particles in the one more liquid sample. The extraction system may comprise means to flush the packed bed column with at least one solvent and to collect the solvent comprising aerosol particles from the packed bed. The at least one solvent may comprise at least one of acetonitrile, methanol, trifluoro acetic acid (TFA), isopropanol (IPA), the remaining being water. The one or more solvents may comprise between about 50 vol.-% and about 70 vol. % acetonitrile in water, between about 50 vol.-% and about 70 vol. % isopropanol in water, and between about 0.05 vol.-% TFA in water. The analytical device may comprise at least one of PCR, ELISA, rt-PCR, mass spectrometer (MS), MALDI-MS, ESI-MS, and MALDI-TOFMS, and LC-MS/MS. The aerosol particles in exhaled breath may comprise at least one of microbes, viruses, metabolite biomarkers, lipid biomarkers, and proteomic biomarkers characteristic of the respiratory disease.

Disclosed is an exemplary method for monitoring the status of a patient infected with a respiratory disease and connected to a ventilator to assist the breathing of the infected patient, the method comprising providing a sample collection system removably connected to the exhaled air tubing of the ventilator provided to assist the breathing of the infected patient, the system comprising one or more sample capture elements comprising a packed bed column in each to selectively capture aerosol particles in the exhaled air produced by the patient wherein the aerosol particles are characteristic of the respiratory disease, and a pump in fluid communication with the sample capture element and configured to draw the exhaled air aerosol into the sample capture element, extracting the captured aerosol particles from the packed bed column into one or more liquid samples, and analyzing the aerosol particles in the one or more liquid samples to determine the presence or absence of the respiratory disease. The exemplary method may further comprise the step of washing the column using at least one of 70% ACN, water, and 0.05% TFA prior to removably connecting the sample collection system to the exhaled air tubing of the ventilator. The extracting step may comprise flushing the packed bed column with about 50 vol.-% ACN and then with about 70 vol.-% IPA. The exemplary method may further comprise a sample processing step comprising, mixing the one or more samples with a MALDI matrix, and applying the one or more mixed samples and MALDI matrix to one or more sample plates. The exemplary method may further comprise a sample processing step comprising subjecting the one or more liquid sample extracted from the sample extraction system to protein digestion to generate a peptide sample characteristic of the respiratory disease. The sample processing step may further comprise mixing the peptide sample with a MALDI matrix and applying the mixed sample and MALDI matrix to a sample plate. The analyzing step may comprise analyzing the sample plate using at least one of PCR, ELISA, rt-PCR, mass spectrometer (MS), MALDI-MS, ESI-MS, and MALDI-TOFMS, and LC-MS/MS.

Disclosed is an exemplary system for sampling ambient air in an enclosed space for the presence of a respiratory disease and capturing aerosol particles in ambient air comprising a sample collection module comprising one or more sample capture elements comprising a packed bed column in each to selectively capture aerosolized particles from exhaled breath present in ambient air, a nebulizer to humidify ambient air prior to entering the one or more sample capture elements, and a fluidic module comprising at least one of a water pump, a power supply, a controller, an air pump to draw ambient air through the one or more sample capture elements, and a water container in fluid communication with the nebulizer and the water pump, wherein the fluidic module is configured to control the operation of the sample collection module. The fluidic module may further comprise at least one of a $CO_2$ sensor and a particle counter disposed between the sample capture element and the pump. The sample collection module and the fluidic module may be each disposed in a portable enclosure. The sample collection module and the fluidic module may be configured to be fluidly and electrically coupled with each other using quick connect/disconnect couplings configured to detect proper mechanical and electrical contact and alert a user via at least one of a graphical user interface disposed on one of the enclosures and an audible alarm. The sample collection module and the fluidic module may be disposed in the same portable enclosure. The packed bed column may comprise at least one of resin beads having C18 functional groups on the surface, cellulose beads having sulfate ester functional groups on the surface, and mixtures thereof. The resin beads and cellulose beads may have a nominal diameter of at least about 20 μm. The resin beads and cellulose beads may have a nominal diameter of between about 40 microns and about 200 microns. The nominal flow rate drawn using the pump through each capture element may be at least about 20 L/min. The sample collection module may further comprise a water reservoir disposed in fluid communication with at least one of the water pump and the water container wherein the nebulizer is immersed in water and disposed near the outlet of the reservoir. The nebulizer may be an ultrasonic mist atomizer.

Disclosed is an exemplary system for detecting respiratory disease agents in ambient air comprising a system for sampling and capturing aerosol particles in ambient air as previously disclosed, a sample extraction system to extract the captured aerosol particles characteristic of the respiratory disease from each packed bed column into one or more liquid samples, and an analytical device to analyze the aerosol particles in the one more liquid sample. The extraction system may comprise means to flush each packed bed column with at least one solvent and to collect the solvent comprising aerosol particles from each packed bed. The at least one solvent may comprise at least one of acetonitrile, methanol, isopropanol (IPA), the remaining being water. The one or more solvents may comprise between about 50 vol.-% and about 70 vol. % acetonitrile in water, and between about 50 vol.-% and about 70 vol.-% isopropanol in water. The analytical device may comprise at least one of PCR, ELISA, rt-PCR, mass spectrometer (MS), MALDI-MS, ESI-MS, and MALDI-TOFMS, and LC-MS/MS.

Disclosed is an exemplary method for detecting respiratory disease agents in ambient air in an enclosed space, the method comprising selectively capturing aerosolized particles from exhaled breath in ambient air using one or more sample capture elements comprising a packed bed column in each wherein ambient air is humidified prior to entry to the one or more sample capture elements and drawn into the one or more sample capture elements using an air pump, extracting the captured aerosol particles characteristic of the respiratory disease from each packed bed column into one or more liquid samples, and analyzing the aerosol particles in the one more liquid sample. The packed bed column may comprise at least one of resin beads having C18 functional groups on the surface, cellulose beads having sulfate ester functional groups on the surface, and mixtures thereof. The extracting step may comprise flushing the packed bed column with at least one of acetonitrile, methanol, isopropanol (IPA), the remaining being water. The exemplary may further comprise a sample processing step comprising, mixing the one or more sample with a MALDI matrix, and applying the one or more mixed samples and MALDI matrix to one or more sample plates. The exemplary method may further comprise a sample processing step comprising subjecting the one or more liquid sample extracted from the sample extraction system to protein digestion to generate a peptide sample characteristic of the respiratory disease. The sample processing step may further comprise mixing the peptide sample with a MALDI matrix and applying the mixed sample and MALDI matrix to a sample plate. The analytical device may comprise at least one of PCR, ELISA, rt-PCR, mass spectrometer (MS), MALDI-MS, ESI-MS, and MALDI-TOFMS, and LC-MS/MS.

Disclosed is an exemplary sample capture element to capture aerosolized bacteria and viruses comprising a packed bed column to selectively capture bacteria and virus particles aerosolized in at least one of exhaled breath and ambient air drawn through the packed bed column using a pump wherein the packed bed column comprises at least one of resin beads having C18 functional groups on the surface, cellulose beads having sulfate ester functional groups on the surface, and mixtures thereof wherein the resin beads and cellulose beads have a nominal diameter of between about 40 microns and about 200 microns. The beads may be packed between two porous polymeric frit discs in the packed bed column.

Other features and advantages of the present disclosure will be set forth, in part, in the descriptions which follow and the accompanying drawings, wherein the preferred aspects of the present disclosure are described and shown, and in part, will become apparent to those skilled in the art upon examination of the following detailed description taken in conjunction with the accompanying drawings or may be learned by practice of the present disclosure. The advantages of the present disclosure may be realized and attained by means of the instrumentalities and combinations particularly pointed out in the appendant claims.

DRAWINGS

The foregoing aspects and many of the attendant advantages of this disclosure will become more readily appreciated as the same becomes better understood by reference to the following detailed description, when taken in conjunction with the accompanying drawings, wherein:

FIG. 1. Schematic diagram of an exemplary exhaled breath sample collection system comprising a packed bed column.

Figure 2:
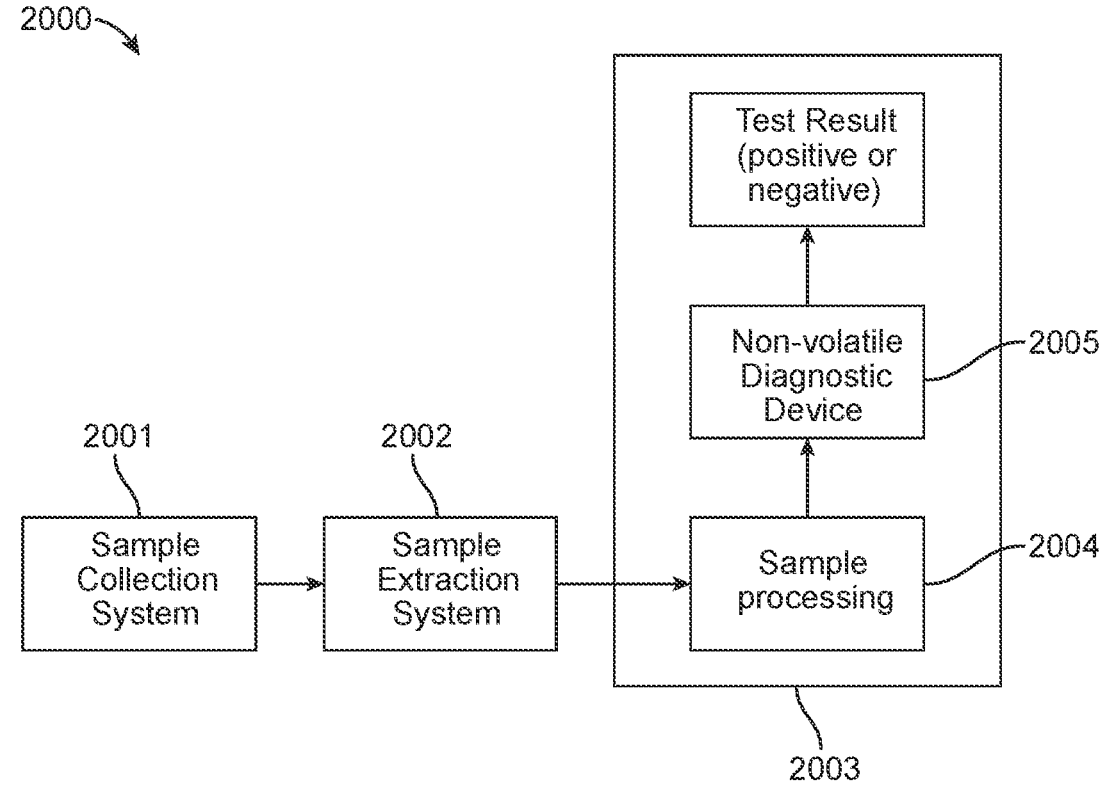

FIG. 2. Schematic diagram of an exemplary diagnostic system for respiratory diseases comprising a sample collection system.

Figure 3:
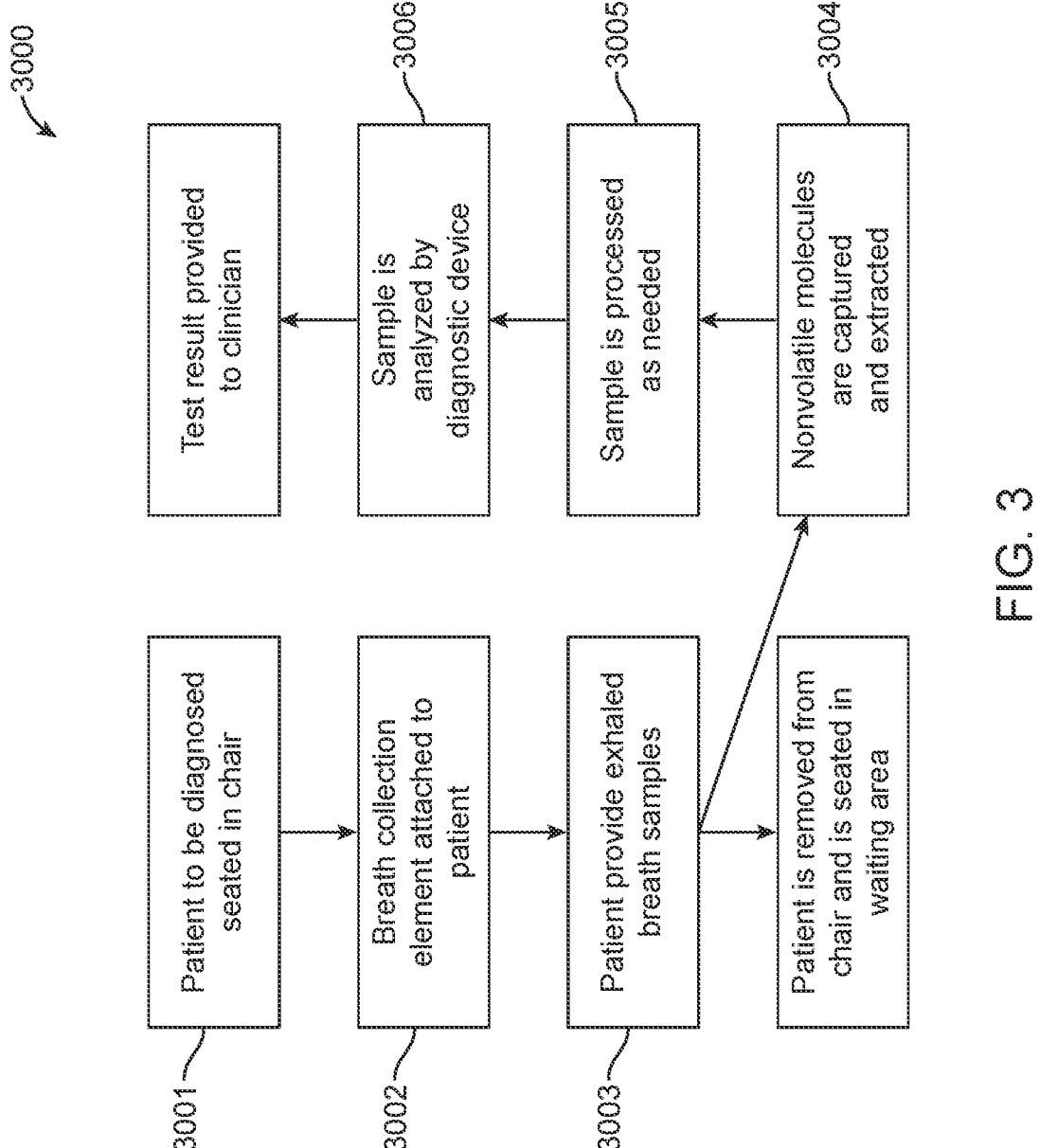

FIG. 3. Schematic diagram of an exemplary diagnostic method using a system that comprises a packed bed column.

Figure 4:
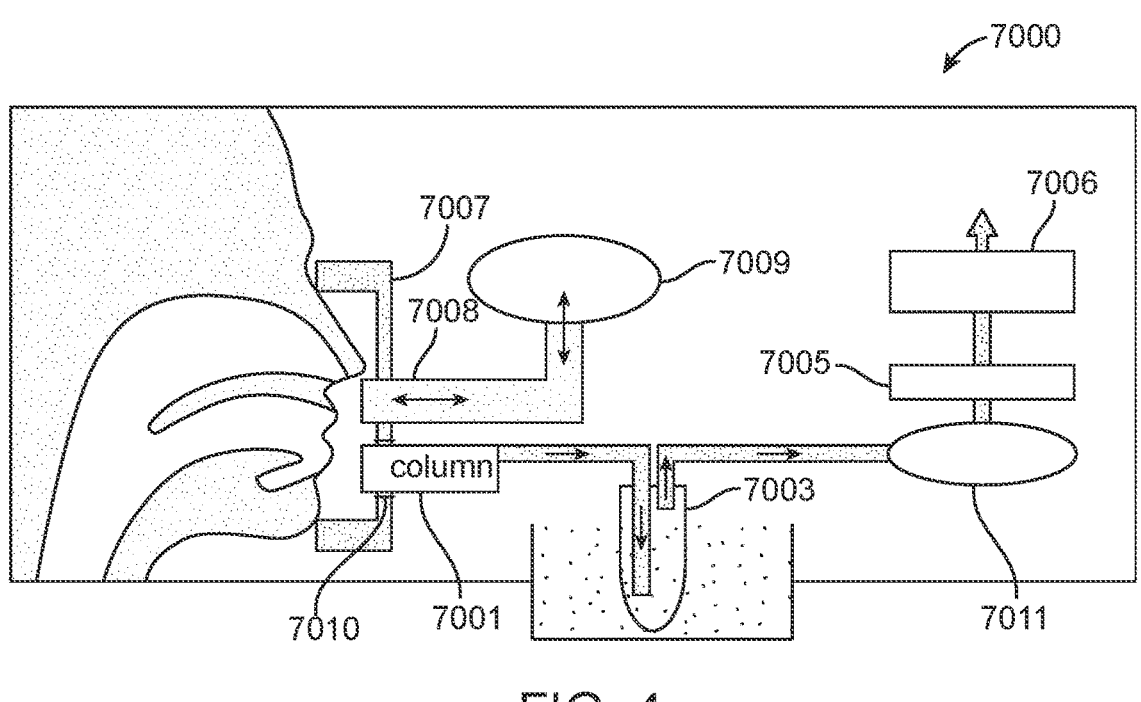

FIG. 4. Schematic diagram of an exemplary exhaled breath sample collection system comprising a packed bed column.

Figure 5:
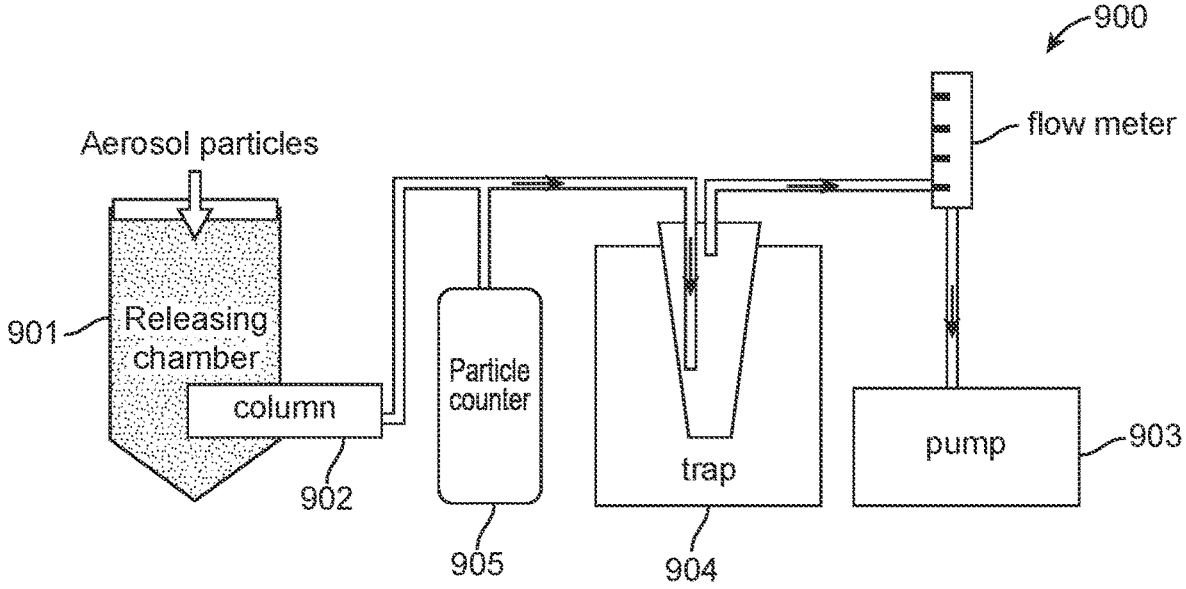

FIG. 5. Schematic diagram of an exemplary ambient aerosol sample collection system comprising a packed bed column.

Figure 6A:
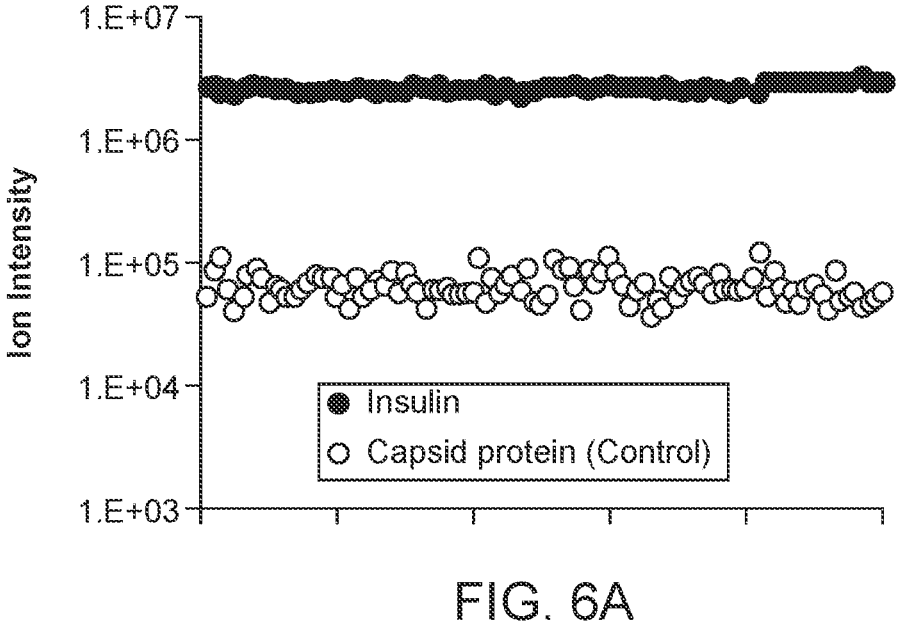
Figure 6B:
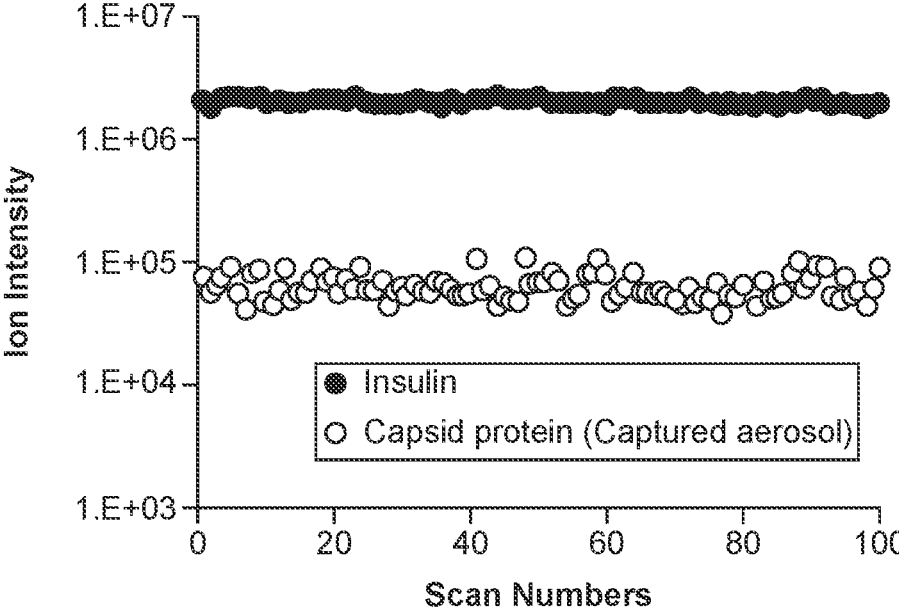

FIGS. 6A-B. Direct infusion mass spectrometry results showing ion intensities of MS2 capsid protein in the control sample (A) and of MS2 capsid protein in the captured aerosol sample (B).

Figure 7A:
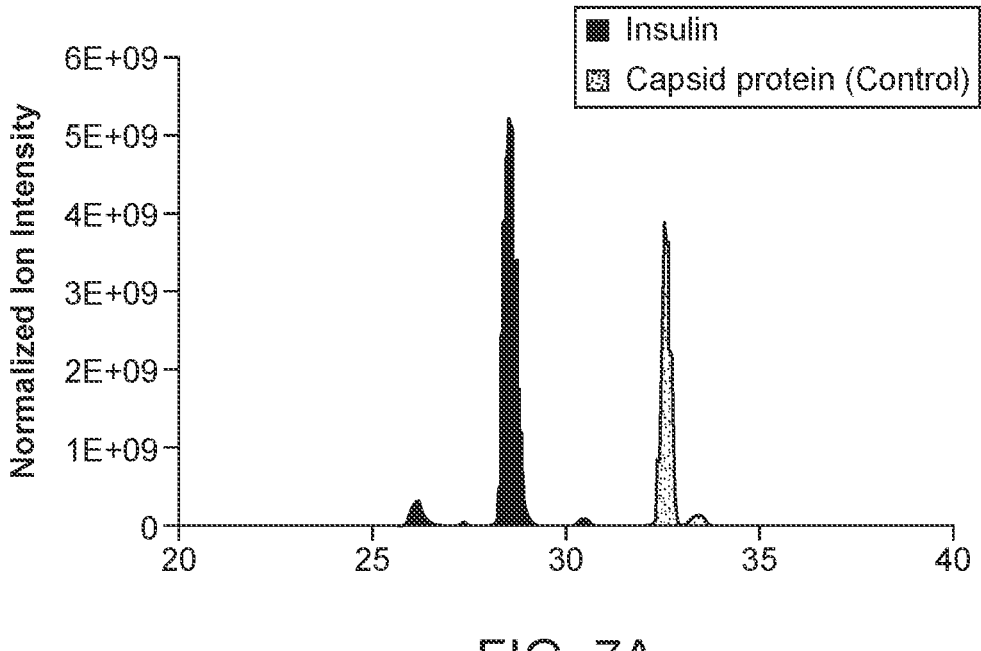
Figure 7B:
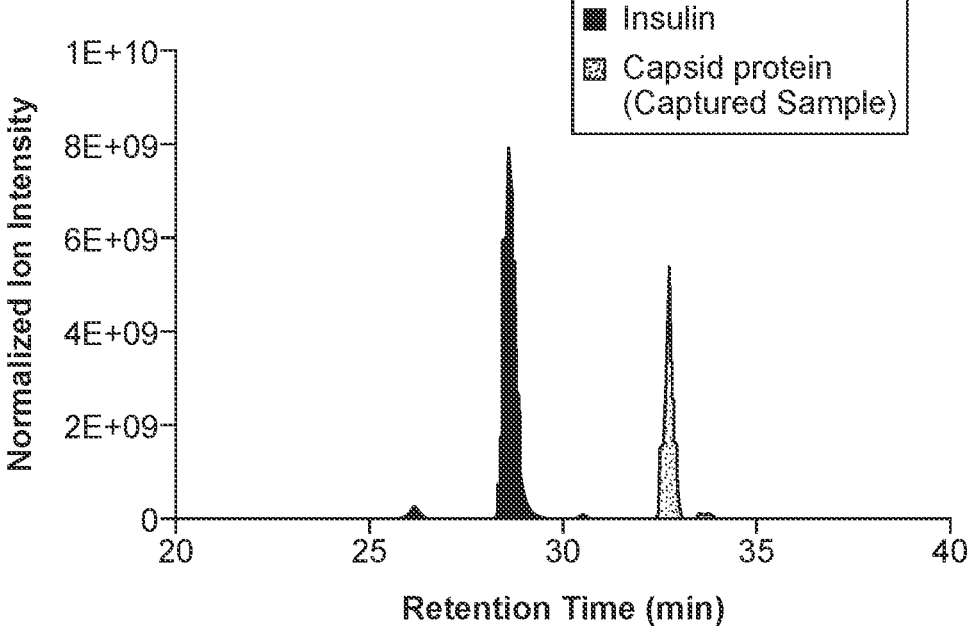

FIGS. 7A-B. Nanoflow-LC mass spectrometry selected ion chromatogram of MS2 capsid protein in the control sample (A) and of MS2 capsid protein in the captured aerosol sample (B).

FIGS. 8A-C. Effect of C18 bead size (A), bead quantity (B), and inlet polymeric frit pore size (C) on flow rate through an exemplary sample capture element.

Figure 9A:
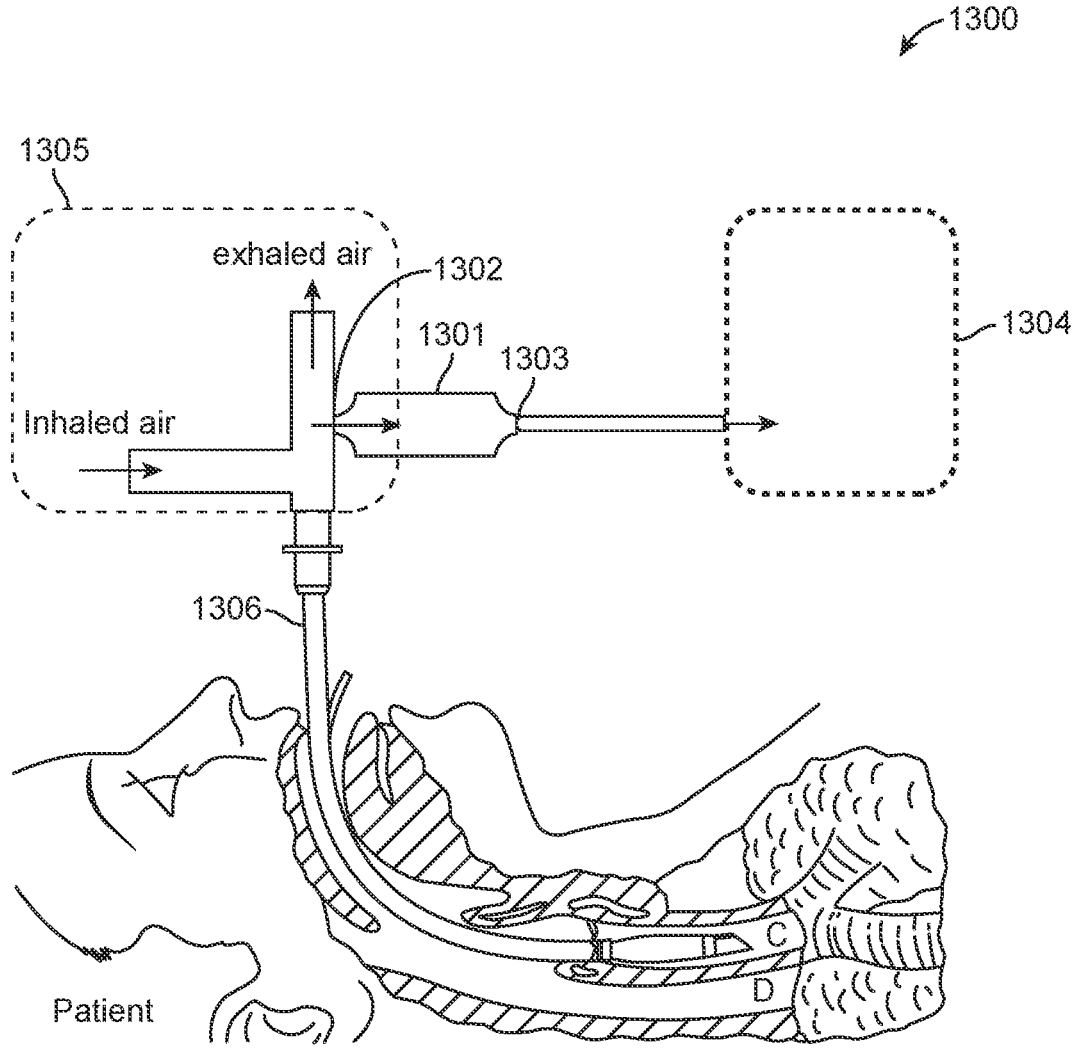
Figure 9B:
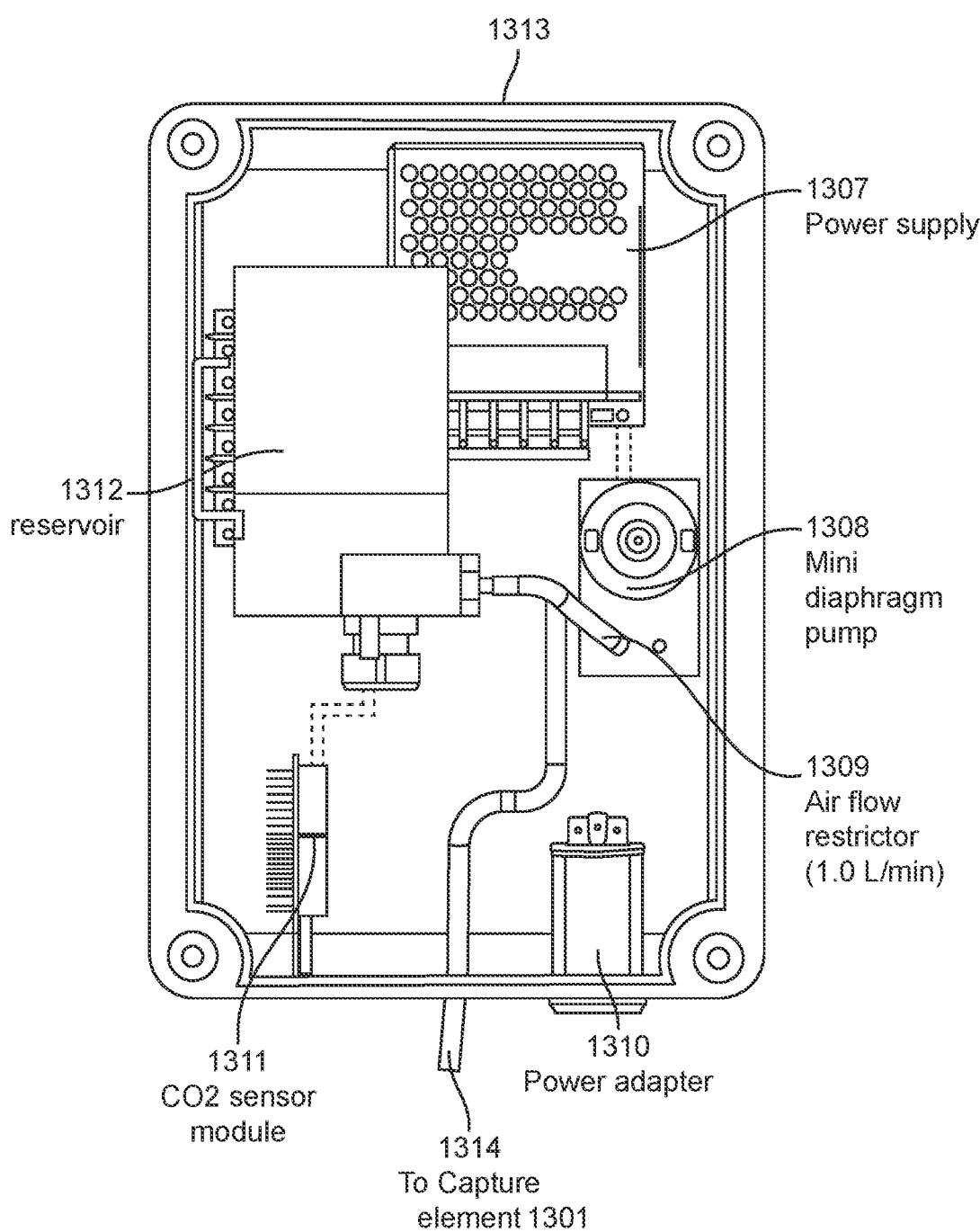

FIGS. 9A-B. (A) Schematic diagram of an exemplary exhaled air aerosol collection system for use with a ventilator connected to patients diagnosed with COVID-19 in intensive care units and (B) schematic diagram of an exemplary portable accessory and control system configured to operate the aerosol collection system connected to a ventilator.

Figure 10:
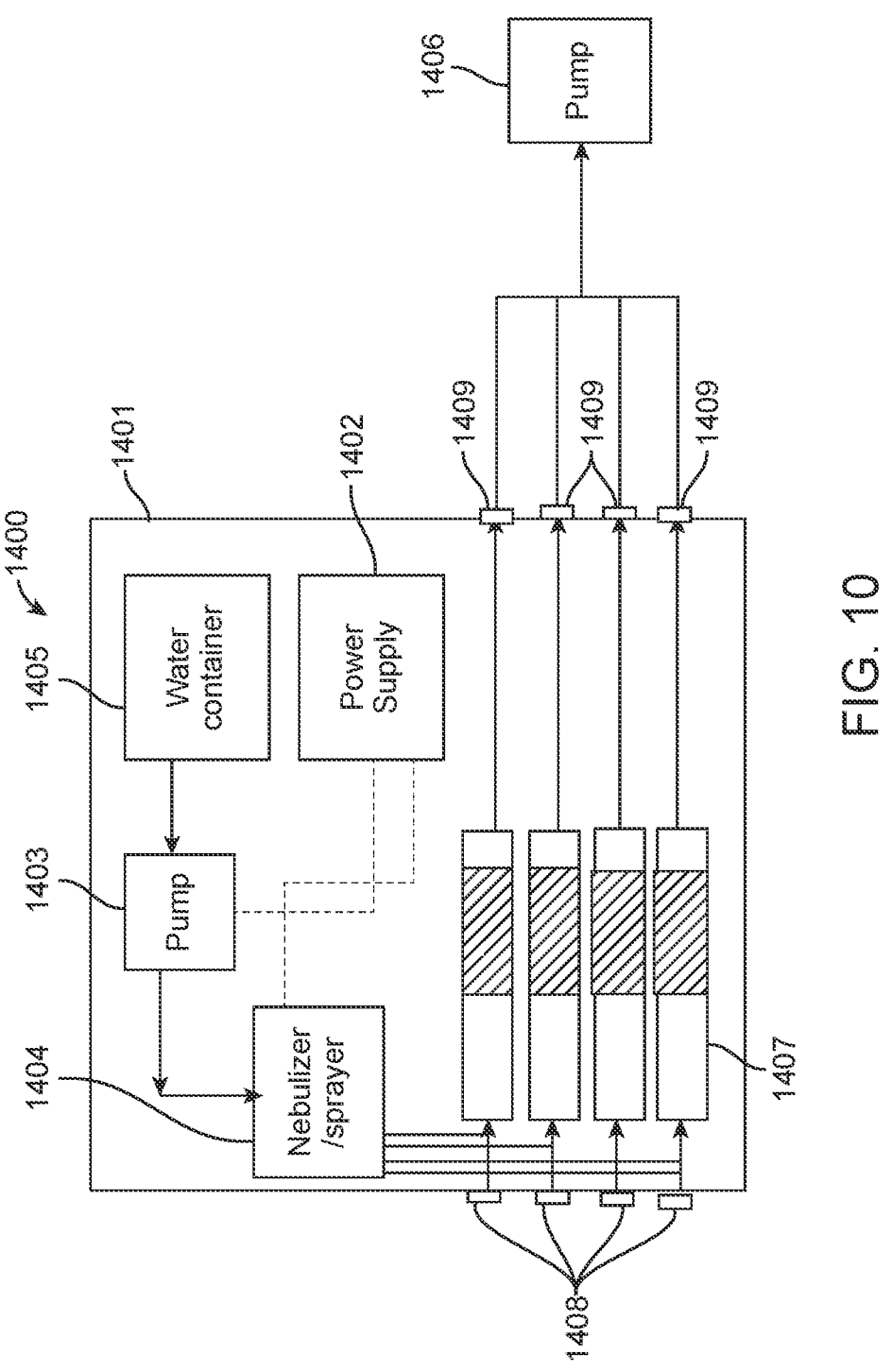

FIG. 10. Schematic diagram of an exemplary aerosol collection system for ambient air sampling.

Figures 11A, 11B:
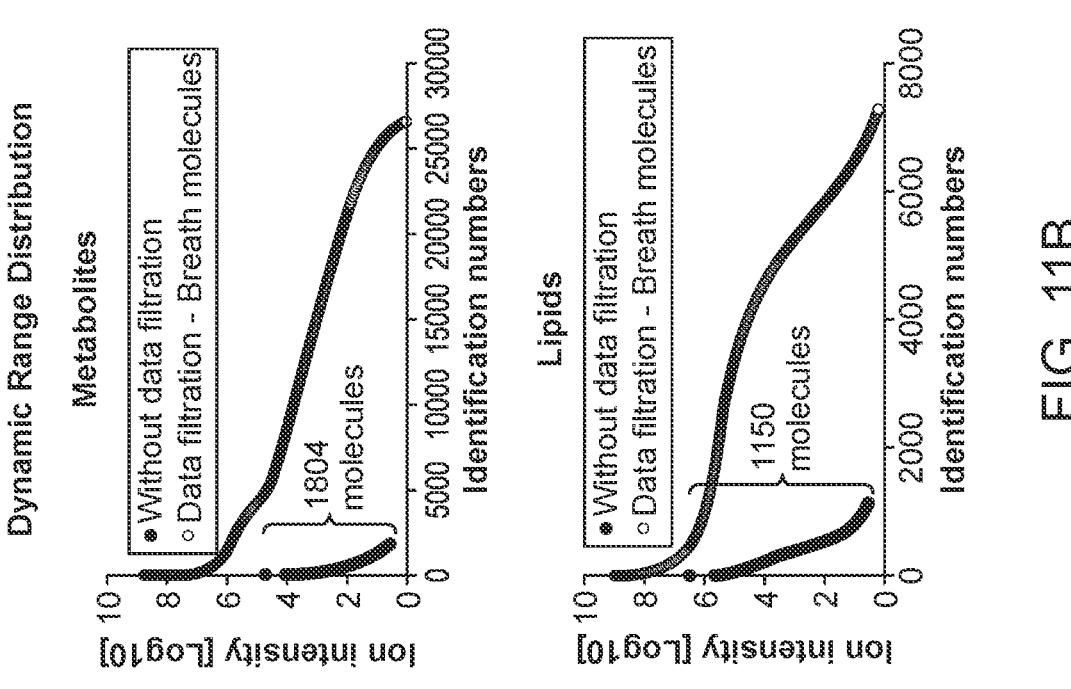
Figure 11C:
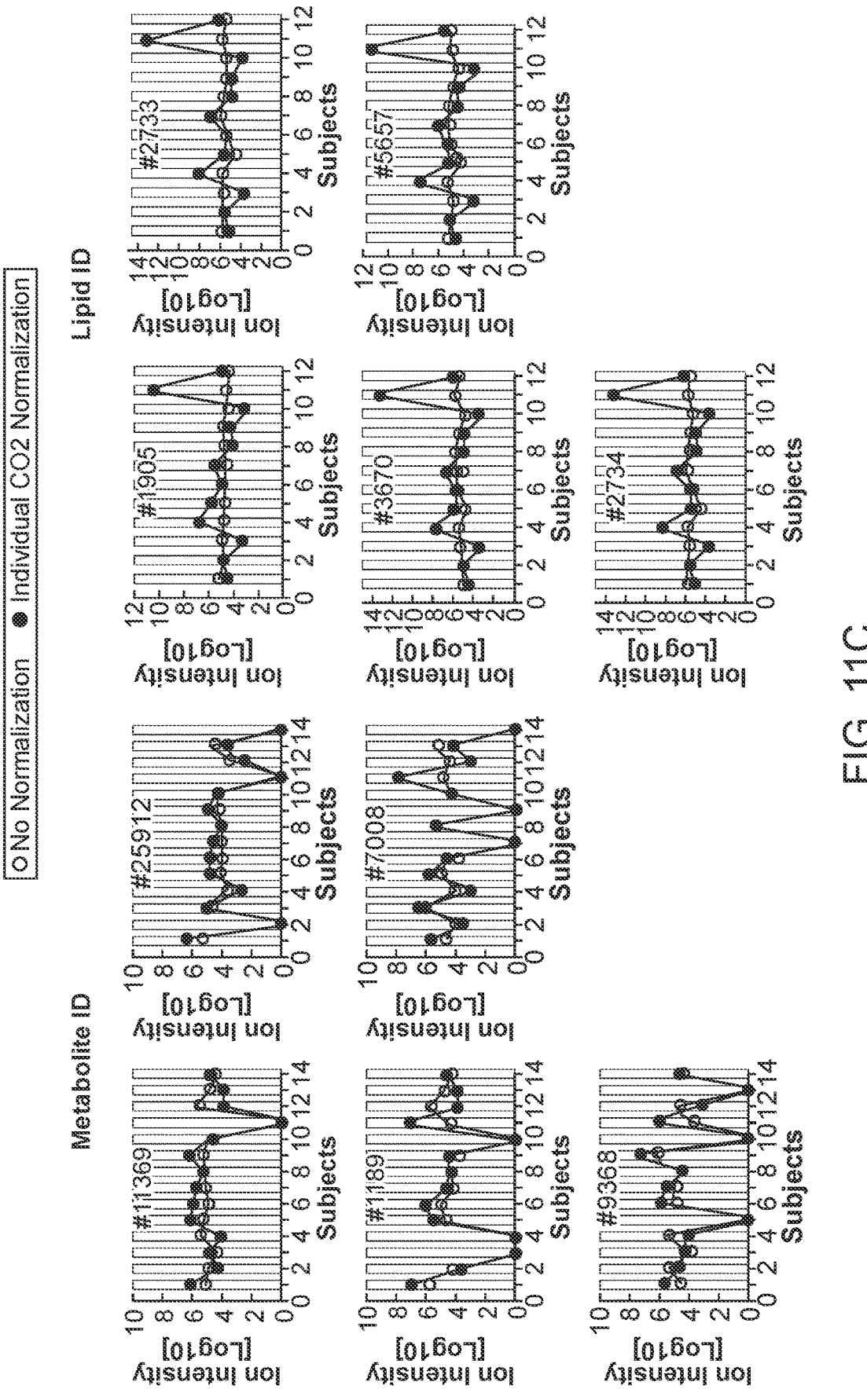
Figures 12A, 12B, 12C, 12D:
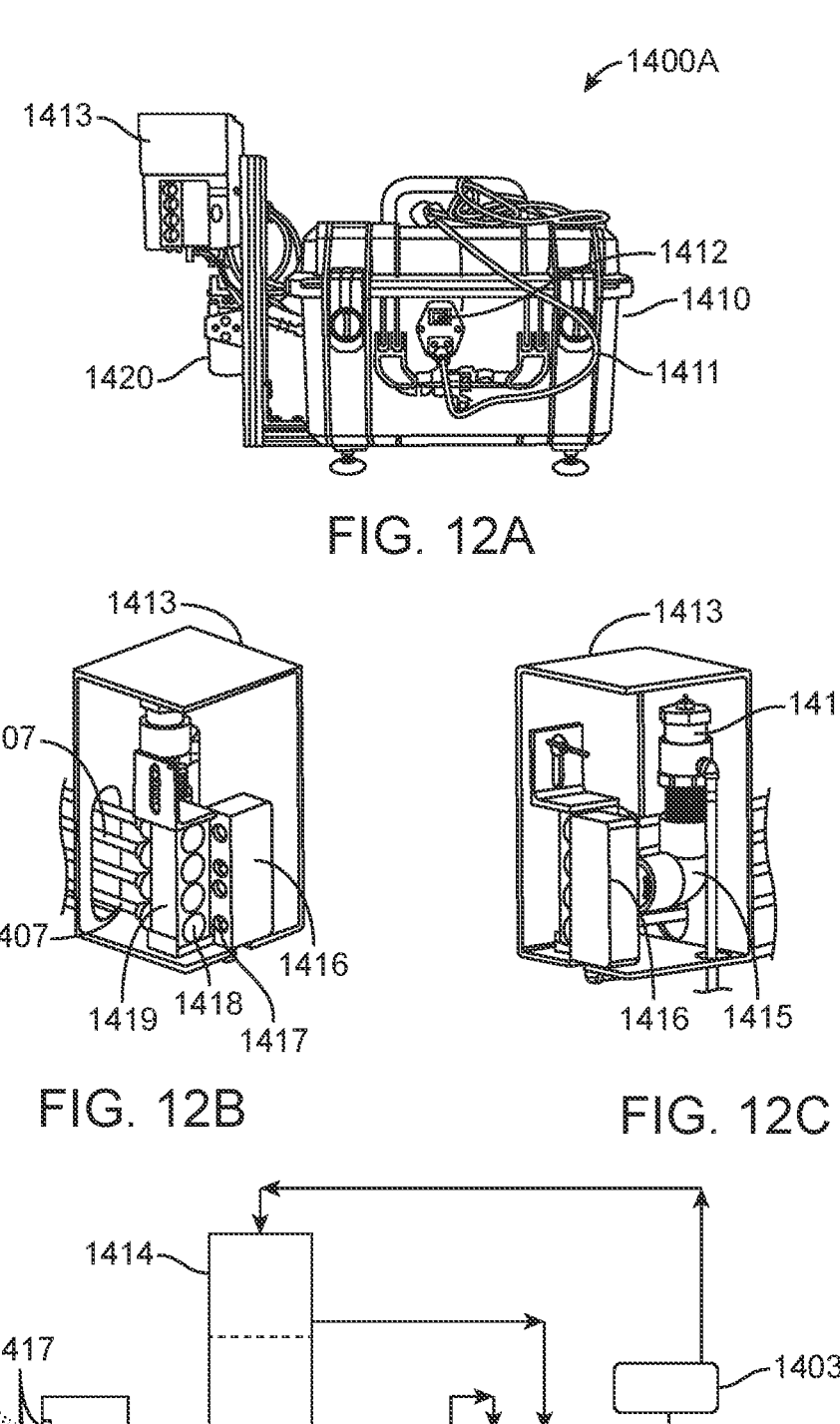

FIGS. 11A-C. PCA and PLS-DA analysis showing segregation of lipids and metabolite biomarkers between breath samples collected from fourteen human subjects and blanks (A), dynamic range distribution with and without data filtering for both lipid and metabolite biomarkers in exhaled breath aerosol samples (B), and ion intensities of lipid and metabolite biomarkers with and without $CO_2$ normalization (C).

FIGS. 12A-D. Isometric drawing of an exemplary aerosol sample collection system for ambient air sampling showing fluidic module and sample collection module (A), isometric views of the fluidic modules (B-C) and schematic diagram of mist generation using the fluidic module.

Figures 13A, 13B, 14:
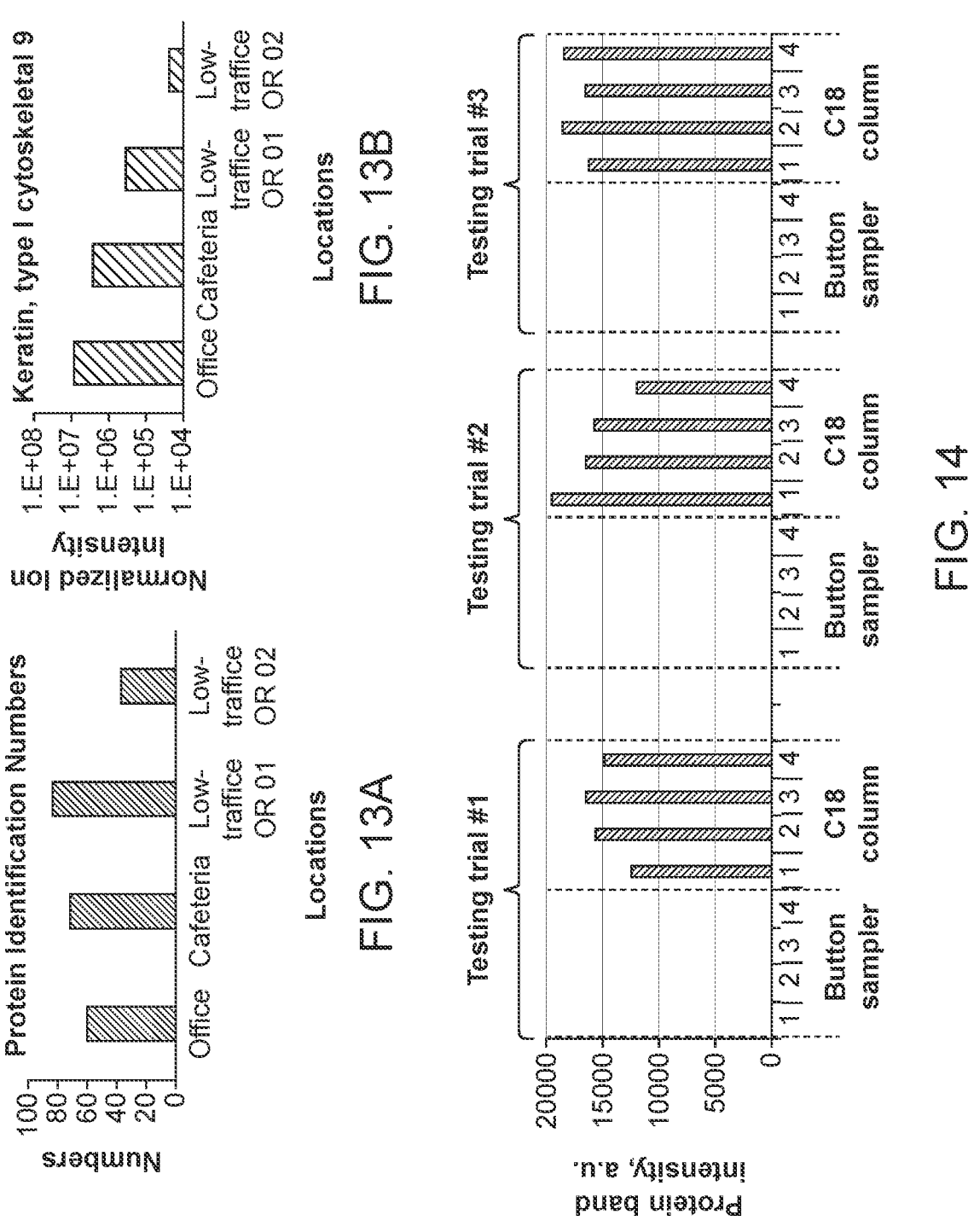

FIGS. 13A-B. Number of proteins identified using bottom-up proteomics of the four ambient air samples (A) and Keratin-9 levels in the four air samples (B).

FIG. 14. Protein blue staining results of aerosolized BSA proteins captured using the exemplary C18 packed bed column sample capture element and a button sampler.

FIGS. 15A-E. MALDI TOF mass spectra of hot acid digested peptides in culture media of SARS-CoV-2 virus sample not treated with exemplary sample capture element (A), MALDI TOF mass spectra with peak assignments of hot acid digested peptides of SARS-CoV-2 virus particles extracted from an exemplary sample capture element (B), distribution of peptide ion intensities constructed using bottom-up proteomics of SARS-CoV-2 sample (C), distribution of peptide ion intensities constructed using bottom-up proteomics of SARS-CoV-2 virus particles extracted from an exemplary sample capture element (D), and peptide mass fingerprint of SARS-CoV-2 virus particles extracted from an exemplary sample capture element using Mascot database search using different allowed missed site cleavage numbers (E).

All reference numerals, designators and callouts in the figures are hereby incorporated by this reference as if fully set forth herein. The failure to number an element in a figure is not intended to waive any rights. Unnumbered references may also be identified by alpha characters in the figures and appendices.

The following detailed description includes references to the accompanying drawings, which form a part of the detailed description. The drawings show, by way of illustration, specific embodiments in which the disclosed systems and methods may be practiced. These embodiments, which are to be understood as "examples" or "options," are described in enough detail to enable those skilled in the art to practice the present invention. The embodiments may be combined, other embodiments may be utilized, or structural or logical changes may be made, without departing from the scope of the invention. The following detailed description is, therefore, not to be taken in a limiting sense and the scope of the invention is defined by the appended claims and their legal equivalents.

In this disclosure, aerosol generally means a suspension of particles dispersed in air or gas. "Autonomous" diagnostic systems and methods mean generating a diagnostic test result "with no or minimal intervention by a medical professional." The U.S. FDA classifies medical devices based on the risks associated with the device and by evaluating the amount of regulation that provides a reasonable assurance of the device's safety and effectiveness. Devices are classified into one of three regulatory classes: class I, class II, or class III. Class I includes devices with the lowest risk and Class III includes those with the greatest risk. All classes of devices as subject to General Controls. General Controls are the baseline requirements of the Food, Drug and Cosmetic (FD&C) Act that apply to all medical devices. In vitro diagnostic products are those reagents, instruments, and systems intended for use in diagnosis of disease or other conditions, including a determination of the state of health, in order to cure, mitigate, treat, or prevent disease or its sequelae. Such products are intended for use in the collection, preparation, and examination of specimens taken from the human body. The exemplary devices disclosed herein can operate and produce a high-confidence result autonomously, and consequently, has the potential to be regulated as a Class I device. In some regions of the world with high burdens of TB infection, access to medically trained personnel is very limited. An autonomous diagnostic system is preferred to one that is not autonomous.

The terms "a" or "an" are used to include one or more than one, and the term "or" is used to refer to a nonexclusive "or" unless otherwise indicated. In addition, it is to be understood that the phraseology or terminology employed herein, and not otherwise defined, is for the purpose of description only and not of limitation. Unless otherwise specified in this disclosure, for construing the scope of the term "about," the error bounds associated with the values (dimensions, operating conditions etc.) disclosed is +10% of the values indicated in this disclosure. The error bounds associated with the values disclosed as percentages is +1% of the percentages indicated. The word "substantially" used before a specific word includes the meanings "considerable in extent to that which is specified," and "largely but not wholly that which is specified." Unless otherwise specified, the concentration of chemicals, solvents and the like disclosed as a percentage refer to vol.-%.

DETAILED DISCLOSURE

Breath aerosol particles contain a variety of nonvolatile organic biomolecules such as metabolites, lipids, and proteins. Further, the nonvolatile molecules have a wide particle size distribution ranging from a sub-micron size to about 10 microns in size. Breath collection and disease diagnostic systems and methods that can efficiently capture different types of nonvolatile molecules of different particle sizes from exhaled breath are required. Particular aspects of the invention are described below in considerable detail for the purpose for illustrating the compositions, and principles, and operations of the disclosed methods and systems. However, various modifications may be made, and the scope of the invention is not limited to the exemplary aspects described.

An exemplary diagnosis system 2000 (FIG. 2) based on exhaled breath analysis ("EBA") may comprise a breath sample collection system 1000 disposed in fluid communication with a sample extraction system 2002 and an analysis system 2003.

An exemplary exhaled breath sample collection system 1000 (FIG. 1) may comprise a sample capture element 1001 comprising a packed bed column to selectively capture breath aerosol comprising nonvolatile organisms including, but not limited to bacteria and viruses, and molecules including small molecules, lipids, and proteins on very high efficiency adsorbent materials. A trap 1003 is in fluid communication with column 1001 using tubing 1002. Trap 1003 may be made of glass or plastic material. Trap 1003 may be cooled to below ambient temperature using an ice bath or other suitable means. Trap 1003 may be used to collect water vapor, other volatile (check) and nonvolatile molecules that may pass through the collection column as exhaled breath condensate (EBC). During breath analysis of a patient breathing using a ventilator, sample capture element 1001 may be removably connected to the capnography port on the respirator tubing of a ventilator, placing it very near the outlet or at the outlet from the patient's lungs. During breath analysis of a normally breathing person, element 1001 may be removably connected to a mouthpiece (not shown) into which the patient is instructed to breathe or otherwise execute a breath maneuver previously disclosed herein. For example, capture element 1001 may be removably connected downstream (at the outlet) of a breath collection element 1007 (FIG. 1) such as a first aid CPR rescue mask (e.g., as supplied by Dixie USA EMS Supply Co., Model Number EVR-CPR01) worn by the patient during breath analysis. A flow splitter 1008 may be disposed between breath collection element 1007 and capture element 1001 to divide the flow of exhaled breath such that a first portion of exhaled breath is directed to capture element 1001 and a second portion towards a HEPA filter 1009. Flow splitter 1008 may be integrated into collection element 1007. Further, a large particle trap 1012 may be disposed upstream of capture element 1001 to remove large particles of breath condensate (greater than about 10 µm) from the exhaled breath stream prior to entering capture element 1001. Pump 1006 may be used to pull exhaled breath into the packed bed column in capture element 1001. An exemplary pump 1006 is a portable diaphragm pump (e.g., Parker Hannifin Corp., Part No.: D737-23-01). The flow rate out of pump 1006 may be adjusted using needle valve 1005 to achieve a desired flow rate. Check valve (one-way flow valve) 1011 may be disposed between pump 1006 and capture element 1001 and is configured to be in an open position only when pump 1006 is pulling exhaled breath through the packed bed column. When there is no flow, valve 1011 is disposed in a closed position. A nominal flow rate of between about 200 ml/min and 600 ml/min may be used. In addition, several capture elements 1001 may be used in parallel to increase the flow rate up to 12 L/min. Further, when one or more capture elements are in collection mode, one or more may be in eluting mode, and the some may be in standby mode. To determine if exhaled breath sample volume was adequate, a $CO_2$ sensor and particle counter (not shown) may be disposed between breath collection element 1007 and sample capture element 1001. $CO_2$ monitoring and particle count allows for an approximation of the proportion of exhaled air volume. A HEPA filter may also be disposed downstream of trap 1003. Capture element 1001 may be cooled using a cooling jacket or other means to reduce the temperature to below ambient temperature to increase the collection efficiency of non-volatile organics particles. The breath sample collection system may further comprise a humidifier 1010 disposed upstream of the inlet to the capture element to humidify exhaled breath and increase the humidity in the packed bed column.

Breath collection element 1007 may comprise a tight-fitting mask configured to receive an individual's face and may be removably attached using straps and the like to the face/head of a patient/individual. The individual may sit in an optional containment booth to isolate the patient's EBA from the ambient air in the testing room or area. Element 1007 may be used to collect and direct breath aerosol particles emitted though the mouth and nose of patient into capture element 1001 using pump 1006 as previously described without depositing the aerosol particles on the walls of element 1007. Element 1007 may be disposable to limit the risk of a patient becoming contaminated or infected with a pathogen emitted by a previous patient. Alternatively, element 1007 may be reusable, in which case it may be sterilized.

The exemplary packed bed column in capture element 1001 may comprise Hamilton PRP-C18 resin beads as supplied by Sigma Aldrich and other vendors. The bed may be held in place between two porous filter plates such as frit discs. For example, a polyethylene disc having an average pore size of above 35 μm may be placed upstream of the bed and a polyethylene disc having an average pore size of 10 μm (Boca Scientific, Dedham, MA) may be placed downstream of the bed. The 35 μm frit disc allows a faster air flow rate while the smaller 10 μm frit disc traps all the C18 resin well. In an exemplary element 1001, the packed bed may comprise about 25 mg of C18 resin beads having a nominal diameter between about 12 μm and about 20 μm. Non-volatile organic components in exhaled breath removably interact with the C18 functional groups on the beads and are trapped. Water, volatiles and other hydrophilic molecules pass through the bed and may be trapped in glass trap 1003.

Besides C18 functional groups, other functional groups that show affinity to nonvolatile molecules may be used as adsorbents in the column immobilized on solid phase beads. The solid phase beads may be made of polymers and particles such as resins, cellulose, silica, agarose, and hydrated $Fe_3O_4$ nanoparticles. Adsorbent materials may comprise other functional groups that include, but are not limited to, octadecyl, octyl, ethyl, cyclohexyl, phenyl, cyanopropyl, aminopropyl, 2,3-dihydroxypropoxypropyl, trimethyl-aminopropyl, carboxypropyl, benzenesulfonic acid, and propylsulfonic acid disposed on solid phase beads. Functional groups may also comprise at least one of ion exchange phases, polymer phases, antibodies, glycans, lipids, DNA and RNA.

Exemplary diagnosis system 2000 (FIG. 2) may comprise a breath sample collection system 2001 disposed in fluid communication with a sample extraction system 2002 and an analysis system 2003. Sample collection system 2001 may comprise exemplary sample collection system 1000 (FIG. 1) as previously described. Sample extraction system 2002 may be used to extract the trapped non-volatile organics from the packed bed column in system 1000 and may be disposed in-line or off-line in system 2000. When system 2002 is disposed off-line, at the conclusion of exhaled breath sample collection, capture element 1001 may be removed from system 1000 and eluted with an organic solvent in extraction system 2002 to remove non-volatile organics from the packed bed column. Exemplary organic solvents include, but are not limited to, about 50-70% acetonitrile in water to extract trapped non-volatile organics (strongly polar non-volatile organic molecules, proteins and the like) from the packed bed column. The extraction may be repeated using the same or another solvent, that includes, but is not limited to 50-70% isopropanol in water to extract less polar lipid molecules from the packed bed. Other organic solvents include between about 50% and about 70% methanol in water, and about 50% methanol in about 50% chloroform. When system 2002 is disposed in-line, at least one of a $CO_2$ sensor and particle counter may be disposed upstream of extraction system 2002. System 2002 may comprise a solvent vessel, a pump to transfer the solvent from the solvent to packed bed column and a vessel to collect the solvent comprising the non-volatile biomarkers into another vessel or cup. Alternately, system 2002 may comprise an injector to inject solvent into the packed bed column and collect the extract liquid comprising non-volatile organics and biomarkers in a suitable cup or vessel, or other laboratory tubes having a small volume. The captured sample in solvent may be further processed and analyzed in analysis system 2003.

Analysis system 2003 may comprise sample processing system 2004 and at least one diagnostic device 2005. Sample processing system 2004 may comprise elements necessary to perform one or more of the following steps:

(a) Placing the sample in at least one of a cup, a vial and a sample plate. For example, the Series 110A Spot Sampler (Aerosol Devices) uses 32 well plates with circular well shape (75 μL well volume) or teardrop well shape (120 μL well volume) which are heated to evaporate the solvent and excess fluid/liquid in the sample to concentrate the sample;

(b) Placing the sample in a cup and exposed to a source of vacuum or freeze-drying device to cause the solvent to evaporate to concentrate the sample; and, (c) hot digestion of proteins and virus particles The samples may be centrifuged to remove chemical contamination particles. Many diagnostic devices may be adapted for use in analysis system 2003 that include, but are not limited to, devices that perform genomics-based assays (such as PCR, rt-PCR and whole genome sequencing), biomarker recognition assays (such as ELISA), and spectral analysis such as mass spectrometry (MS). Of these diagnostic devices, MS is preferable on account of its speed of analysis. The MS techniques that are preferable for biomarker identification are electrospray ionization (ESI) and matrix assisted laser desorption ionization (MALDI) time of flight MS (TOFMS). ESI may be coupled to high resolution mass spectrometers. MALDI-TOFMS devices may be compact, lightweight, consume less than 100 watts of power and provide sample analysis in less than 15 minutes. MALDI-TOFMS is a preferred diagnostic device for point-of-care diagnostics suitable for ACF. The sample must be dry before it is inserted into the vacuum chamber of the MS and subjected to laser pulses from an ultraviolet laser. This interaction between the sample and the laser creates large, informative biological ion clusters that are characteristic of the biological material. When a concentrated sample is provided by sample processing system 2004 comprising only trace levels of water or trace levels organic solvents such as 50% to 70% of one of acetonitrile, methanol, and isopropanol in water, sample analysis using MS may take less than 5 minutes (including the sample preparation) because less time is needed to evaporate the water from the sample.

MALDI-TOFMS may be used to identify live/active agents that include, but are not limited to, *B. anthracis* spores (multiple strains), *Y. pestis*, *F. tularensis*, Venezuelan equine encephalitis virus (VEE), Western equine encephalomyelitis virus (WEE), Eastern equine encephalitis virus (EEE), botulinum neurotoxins (BoNT), *staphylococcus* Enterotoxin (SEA), Staphylococcal enterotoxin B (SEB), ricin, abrin, Ebola Zaire strain, aflatoxins, saxitoxin, conotoxins, Enterobacteria phage T2 (T2), HT-2 toxins (HT2), cobra toxin, biothreat simulants including *B. globigii* spores, *B. cereus* spores, *B. thuringiensis* Al Hakam spores, *B. anthracis* Sterne spores, *Y. enterocolitica, E. coli*, MS2 virus, T2 virus, Adenovirus and nonvolatile biochemical threats including NGAs (nonvolatile), bradykinin, oxytocin, Substance P, angiotensin, diazepam, cocaine, heroin, and fentanyl. Further, the exemplary systems and methods disclosed herein may be used to achieve accurate detection and identification of SARS-CoV-2 from human breath samples.

In "matrix assisted laser desorption ionization" (MALDI), the target particle (analyte) is coated by a matrix chemical, which preferentially absorbs light (often ultraviolet wavelengths) from a laser. In the absence of the matrix, the biological molecules would decompose by pyrolysis when exposed to a laser beam in a mass spectrometer. The matrix chemical also transfers charge to the vaporized molecules, creating ions that are then accelerated down a flight tube by the electric field.

Microbiology and proteomics have become major application areas for mass spectrometry; examples include the identification of bacteria, discovering chemical structures, and deriving protein functions. MALDI-MS has also been used for lipid profiling of algae. During MALDI-MS, a liquid, usually comprised of an acid, such as trifluoroacetic acid (TFA), and a MALDI matrix chemical such as alpha-cyano-4-hydroxycinnamic acid, is dissolved in a solvent and added to the sample. Solvents include acetonitrile, water, ethanol, and acetone. TFA is normally added to suppress the influence of salt impurities on the mass spectrum of the sample. Water enables hydrophilic proteins to dissolve, and acetonitrile enables the hydrophobic proteins to dissolve. The MALDI matrix solution is spotted on to the sample on a MALDI plate to yield a uniform homogenous layer of MALDI matrix material on the sample. The solvents vaporize, leaving only the recrystallized matrix with the sample spread through the matrix crystals. The acid partially degrades the cell membrane of the sample making the proteins available for ionization and analysis in an MS.

Other MALDI matrix materials include 3,5-dimethoxy-4-hydroxycinnamic acid (sinapinic acid), α-cyano-4-hydroxycinnamic acid (α-cyano or α-matrix) and 2,5-dihydroxybenzoic acid (DHB) as described in U.S. Pat. No. 8,409,870.

Further, the volatile organic compounds collected in trap 1003 (FIG. 1) may be warmed using a heater, to drive off the volatile compounds into a diagnostic device such as GC-MS, GC-IMS, volatile ion chromatography, or any other type of analysis method suitable for analyzing volatile organic compounds.

Virus (e.g., SARS-CoV-2) detection is centered on detection of viral proteins, which is a difficult challenge. An exemplary method for virus detection may comprise a glycan-based capture matrix (beads) to pull the target virus out of the background matrix (e.g., other non-virus biomolecule, contaminants). An aliquot of the sample which may contain a virus, for example, collected using sample collection system 1000, which may also comprise other background contaminants, may be applied to a bead carrying the capture probe. At least one of glycan, heparin, and carbohydrates may be used as capture materials or probes bound on resin beads or some other types of beads. An optional washing step may be used to remove any nontargeted-virus contaminants. The concentrated and purified virus may be eluted off the beads using suitable solvents into a sealed heating chamber containing an organic acid which may comprise formic acid or acetic acid and heated to 120° C. for about 10 minutes to digest the proteinaceous toxin down into specific peptide fragments. This hot acid protein digestion protocol cleaves the protein at aspartic acid residues creating a highly reproducible peptide pattern. The capture and digestion processes described may be accomplished with antibodies and enzyme, respectively. Using this exemplary sample processing for MALDI-TOFMS, sensitivity for ricin biotoxin of better than 100 ng/mL (with S/N of about 50:1) in clean buffer was achieved. At S/N (signal to noise ratio) of 3:1, limits of detection (LOD) of <10 ng/mL may be achieved. For the 1 μL samples used in the MALDI-TOFMS analytical systems, about 10 ng/mL LOD equates to a total mass of about 10 pg ($10^{12}$ g) on the probe, which is equivalent to about 20,000 viral particles. An exemplary microfluidic sample processing system to implement the method disclosed above may be configured to analyze samples collected from the air or from other sources such as nasal swabs. The glycan-based capture column and other microfluidics components may be reusable. Large fluid reservoirs containing buffer, weak acids, and alcohols may be employed to provide sufficient capacity to measure 100's of samples in one channel of the system. Multiple systems may be run in parallel to process multiple samples simultaneously. Since no fragile and expensive biomolecular reagents are required, the system is cost effective.

Hot acid digestion cleaves the proteins reproducibly at aspartic acid residues creating known peptide sequences with known masses. These peptide mass distributions are characteristic of the progenitor proteins. Thus, digestion provides outstanding specificity if the proteins of interest are largely separated from background materials. Furthermore, the peptide mass distribution is directly determined by the genome, accounting for post-translational modifications. As soon as a new virus is isolated, it is rapidly sequenced. The RNA sequence of the SARS-CoV-2 virus may be used to accurately predict the protein sequences with modern bioinformatics tools (ExPASy bioinformatics portal). These proteins can then be "digested" in silico using bioinformatics tools to create a theoretical peptide map. Thus, the peptides that arise from SARS-COV-2 digestion can be predicted and compared to experimental data to generate a specific MALDI TOFMS signature of the organism. Reports suggest that the predominant proteins in SARS-CoV are characterized by about 46 kDa nucleocapsid protein and the 139 kDa spike proteins. Other proteins in reasonable abundance are E, M and N proteins.

Detection specificity of a target virus will require some level of background removal, particularly if the background contains other proteins. If large amounts of exogenous proteins are present, the peptide map could be dominated by non-target peptides. As previously described, affinity capture probes for the virus toxins based on glycan-decorated agarose beads may be used to readily clean up the toxins, even in large excess of background proteins, and other biomolecules. When analyzing exhaled breath for virus targets such as SARS-CoV-2, other human proteins in breath may interfere with detection specificity. An affinity-based cleanup of the sample is required to ensure highest specificity. Virus detection may require bead materials that provide more selective affinity compared to the glycan-decorated beads previously described. For example, dextran-based adsorbents may be used for purifying viruses, including coronaviruses, but the affinity of this resin for the target virus may not be satisfactory. As an alternative, carbohydrates may be used for viral and protein purification including target viruses such as SARS-CoV and SARS-CoV-2. Further heparin, and heparan sulfate may be used as binding agents bound to resin beads. Heparin covalently linked to sepharose beads (GE Healthcare Life Sciences, Heparin Sepharose 6 Fast Flow affinity resin Product #17099801) may be used instead of glycan capture beads. This resin may enable bead-based capture affinity capture system for collecting virus particles from exhaled breath. In an exemplary diagnostic system, exhaled breath samples may be pulled through a capture bed in a sample collection system 1000, collecting particles from the breath. The resin beads (bed) may be washed to remove any background material. The viral particles adsorbed to the beads would then be eluted off using high concentration of acid solution, such as at least one of about 12.5% acetic acid, about 5% TFA, about 5% formic acid and about 10% HCl, into the hot acid digestion chamber to generate the characteristic peptides. The peptide samples may be mixed with MALDI matrix and deposited onto as suitable substrate for MALDI TOFMS analysis. The samples may also be deposited on a suitable substrate or disk that is precoated with MALDI matrix.

FIG. 3 is a schematic diagram of an exemplary diagnostic method 3000 using exemplary system 2000. Exemplary method 3000 may be used to perform autonomous point-of-care diagnosis based on exhaled breath. In step 3001, the individual (or patient) may be directed to be seated; the chair may optionally be located in a containment booth. In step 3002, sample breath collection element 1007 may be removably fitted to the individual's head. The individual is then instructed to breathe or perform one or more predetermined maneuvers 3003 which may include a pre-set number of repetitions. Non-volatile organics in breath are captured using system 1000 and extracted using system 2002 in step 3004 and eluted using suitable solvents. During sample collection, human exhaled breath passes through the column at a predetermined flow rate drawn by a pulling pump. Since nonvolatile molecules contained in the exhaled breath interact with the functionalized beads in capture element 1001 (e.g., C18 functional groups immobilized on resin beads), these molecules are trapped in the column bed in element 1001 while hydrophilic molecules comprising mostly of water and aqueous electrolytes in the breath pass through the column. Nonvolatile organic molecules in human breath a show strong affinity for alkyl chains via intermolecular forces including hydrogen bond and noncovalent interaction. Elution of nonvolatile molecules from the column bed may be accomplished using organic solvent that include, but are not limited to, acetonitrile, methanol, and isopropanol as previously described. The sample may be further processed in step 3005 using component 2004. The type of sample processing depends on the type of diagnostic device and the non-volatile analyte particle of interest. As previously described, a virus sample may be subjected to hot acid digestion chamber to generate characteristic peptides. The peptide samples may be mixed with MALDI matrix and deposited onto as suitable substrate for MALDI TOFMS analysis. The samples may also be deposited on a suitable substrate or disk that is precoated with MALDI matrix. The sample is then analyzed by a diagnostic device in step 3006. When the diagnostic device is MALDI-TOFMS, sample processing may also comprise the steps of plating the sample on to a MALDI-TOFMS sample disk, heating the disk to concentrate the sample, and drying the disk. The sample disk is then analyzed using a MALDI-TOFMS. The TOFMS detectors may be modified to incorporate an ion gate and a reflectron to enable analysis and sequencing of COVID-19 type virus peptides that are fragmented during MALDI-TOF/MS. The spectrum obtained is compared to spectra from samples that were known positives to specific respiratory infections, to spectra in known databases, and also to spectra of samples form patients know to be healthy, and a diagnosis of the patient is generated. The result may then be communicated to a clinician or to the patient.

Once the breath collection element 1007 is attached to the patient, and sample extraction is initiated, the exemplary systems and methods may be preferably autonomous (with the exception of asking the patient to the leave the chair after performing the required maneuvers) and generates a test result of the diagnosis. In the case of virus particles like SARS-CoV-2, the particles are about 0.1 micron in diameter and sensitivities may be between about $10^3$ and $10^4$ viral particles.

Reports suggests that analysis of nose and throat swabs from influenza patients and COVID-19 patients produce viral counts of between about $10^3$ and $10^{10}$ viral particles. Less is known about the viral particles count in the breath of patients. Other reports suggest that influenza patients exhaled>$10^4$ particles in about 30 minutes of breathing. If the output of SARS-CoV-2 is similar to that of influenza, an output of $10^3$ to $10^4$ particles in exhaled breath with a particle collection efficiency of >99.9% should be sufficient to identify the target virus particles in exhaled breath using the exemplary methods and systems disclosed herein. Detection time using the exemplary systems and methods may be between about 10 minutes and 20 minutes include the steps of sample extraction (breathing maneuvers), sample collection, sample processing (digestion) and analysis using a MALDI TOF-MS. This detection time is quite rapid compared to existing detection systems.

An exemplary sample processing component may comprise a hot acid digestion module or cartridge to autonomously extract sample from the packed bed column 1001, perform sample clean-up, conduct the hot acid digestion and provide a sample ready for plating on a MALDI-TOFS sample substrate or disk. The cartridge may be designed for reusability by adding the capability to flush the cartridge between uses.

Disclosed in another exemplary sample collection system 7000 (FIG. 4). Exemplary sample capture element 7001 may comprise a packed bed column comprising C18-bonded resin beads. These resin beads have C18 functional groups immobilized on the surface. Capture element 7001 may be connected or removably installed to a first aid CPR rescue mask 7007 with minor modifications. The stem 7008 of mask 7007 that usually connects to a resuscitation bag may be modified to removably connect to a HEPA filter 7009. The HEPA filter prevents contamination of exhaled breath by contaminants from ambient air. The oxygen inlet 7010 to the mask usually located below the stem and configured to be proximate to the chin of a human subject when a mask is worn by the subject may be modified to removably connect to capture element 7001. Element 7001 may be a removably inserted into mask 7007 through inlet 7010 or otherwise removably connected to or inserted into mask 7007 to form a substantially leak-tight fit with mask 7007. Mask 7007 may comprise elastic bands or ties that may be looped behind the head of a human subject to seal the mask to the face of the patient. Mask 7007 configured as described above prevents direct contact between the mouth and the inlet of the column in element 7001 and minimizes or eliminates contamination of the column inlet by saliva and also maximizes non-volatile organic particle collection from exhaled breath. Trap 7003 immersed in ice water may be installed after (downstream) of capture element 7001. The flow rate (air draw rate) using pump 7006 may be controlled using needle valve 7005 to pull about 600 mL/min. A nominal flow rate of between about 200 ml/min and 600 ml/min may be used. An optional HEPA filter 7011 may be installed between trap 7003 and needle valve 7005. Other fluidic components such as a check valve (see FIG. 1) may be installed in system 7000 to prevent backflow into the column bed in element 7001. $CO_2$ in exhaled breath passes through the column bed in element 7001. To determine if exhaled breath sample volume and/or breathing maneuvers are adequate, a $CO_2$ sensor may be disposed between the outlet of breath capture element 7001 and trap 7003. $CO_2$ monitoring allows for an approximation of the proportion of exhaled air volume. A particle counter may also be installed between the outlet of element 7001 and trap 7003 to detect the size and number for particles exiting the column bed, which may also be used to detect saturation of the bed and breakthrough of nonvolatile organic molecules from the column bed. Exemplary system 7000 may also comprise a capture element 7001 bypass line (not shown) to enable standardization of breath volume prior to routing into the column bed in element 7001. A $CO_2$ sensor and particle counter may also be fluidly connected to the bypass line. The capacity of solid beads immobilized with functional groups in the column bed in capture element 7001 to capture non-volatile organic molecules may be between about 0.05 mg (non-volatile organics)/mg beads and about 0.5 mg/mg. The capacity of C18-bonded resin beads in the column bed in exemplary capture element may be about 0.1 mg/mg. That is, a column bed having 25 mg C18 beads would have the capacity to trap or adsorb about 2.5 mg of non-volatile organic molecules.

Besides C18 functional groups, other functional groups that show affinity to nonvolatile molecules may be used as adsorbents in the column immobilized on solid phase beads such as resin beads. The solid phase beads may be made of polymers and particles such as resins, cellulose, silica, agarose, and hydrated $Fe_3O_4$ nanoparticles. Adsorbent materials may comprise other functional groups that include, but are not limited to, octadecyl, octyl, ethyl, cyclohexyl, phenyl, cyanopropyl, aminopropyl, 2,3-dihydroxypropoxypropyl, trimethyl-aminopropyl, carboxypropyl, benzenesulfonic acid, and propylsulfonic acid disposed on solid phase beads. Functional groups may also comprise at least one of ion exchange phases, polymer phases, antibodies, glycans, lipids, DNA and RNA.

The exemplary system and methods described herein are not necessarily limited in their diagnostic capability to respiratory infections. Lung cancer, for example, may also release biomarkers into the peripheral lung fluid, and these biomarkers would be readily detected by the systems and methods disclosed. Furthermore, because blood comes into intimate contact with the alveolar lining in the lungs, biomarkers of infection and cancer in other parts of the body (beyond the lungs) may be transferred across the alveolar lining and into the peripheral lung fluid, and thus, may be detected by the analysis of EBA. As a result, the scope of the invention is not limited to the detection and diagnosis of respiratory disease. The exemplary systems and methods may be used to capture aerosol chemical particles such a ricin and analyze the particles to prevent a chemical attack threat.

In the exemplary systems and methods described herein, the packed bed column length (L) in sample capture element 1001 is about 3 mm. The nominal internal diameter of the tube is about 7 mm (D). An exemplary packed bed comprising about 25 mg of C18 resin beads having a nominal particle diameter ($D_p$) of between about 12 μm and 20 μm, yields a $L/D_p$ ratio of between about 150 and 250 at a $D/D_p$ ratio of about 350 to about 580. These column parameters were found to prevent undesirable localized flow distributions in the bed to ensure that substantially all resin beads were exposed to the aerosol flow through the bed.

Disclosed are exemplary systems and methods for capture (or collection) of ambient aerosol particles for diagnosis of at least one respiratory disease. An exemplary aerosol collection system 900 (FIG. 5) may comprise an ambient aerosol releasing chamber 901, a sample capture element 902 fluidly and removably connected preferably directly to the releasing chamber. Capture element 902 comprises a packed bed to selectively capture non-volatile organic components such as bacteria and virus particles in the aerosol. Pump 903 is disposed in fluid communication with the sample capture element and is configured to draw the aerosol flow through the sample capture element. The particle capture efficiency of collection system 900 may be at least about 99% for particle sizes that range from about 0.3 μm to about 10 μm that covers the range of most organic particles in ambient air. Although the size of bare virus particles is very small, often as small as 100 nm, the size of exhaled respiratory particles (exhaled breath aerosols, EBA) which may comprise virus particles (e.g., SARS-CoV-2 virus that causes COVID-19) collected from ambient air are often measured to be in size ranging from about 100 nm to about 5 μm. Further, a significant fraction of the aerosol mass is comprised of particles greater than about 2 μm in diameter. The viral particles are typically suspended in aqueous lung fluids that contain water, surfactants, proteins, salts and other chemicals. Particle generation is highest when talking and during other activity which causes deep breathing. After these particles are exhaled, they typically shrink on account of water loss. When subsequently captured using exemplary ambient aerosol collection system 900, most of the EBA mass is expected to comprise of particles of size of between about 1 μm and about 5 μm. Before use, the packed bed column may be washed (or flushed) with about 70% acetonitrile (ACN) followed-by with about 0.05% trifluoroacetic acid (TFA). About 400 μL of 70% acetonitrile and about 400 μL of 0.05% trifluoroacetic acid (TFA) may be used to wash an exemplary column comprising about 25 mg of C18 beads. Further, an exemplary column may be washed once with 70% ACN and thrice with 0.05% TFA. Exemplary column is kept in a moist or wet state prior to use. For a packed bed column comprising about 25 mg of C18 beads, about 100 μL of 0.05% TFA may be used to load the beads after the washing step and both ends of the column may be preferably capped and stored at about 4° C. to avoid freezing.

In another exemplary aspect, a plurality of packed bed columns may be configured as a bundle of columns, for example, as a sample collection cartridge. The cartridge may comprise a suitable inlet distribution element disposed in fluid communication with an aerosol sample flow to distribute the aerosol sample into the plurality of packed bed columns in a substantially uniform manner when flow is drawn through the cartridge using a pump. The cartridge may comprise a suitable outlet distribution element disposed in fluid communication with a pump to draw the aerosol sample through the plurality of packed bed columns. The exemplary sample collection cartridge may be used to capture an aerosol sample using methods and devices for high air flowrate (for example, about 200 L/min to about 500 L/min) collection of exhaled breath aerosols present in indoor air. These methods and devices may be combined with MALDI-TOFMS and highly sensitive and specific on-site genomic analysis suitable for Active Case Finding (ACF) of diseases such as COVID-19 from ambient air samples as disclosed in commonly owned U.S. Prov. patent application Ser. No. 17/586,679 titled "RESPIRATORY DISEASE SURVEILLANCE SYSTEMS AND METHODS USING HIGH FLOWRATE AEROSOL CAPTURE FOR RAPID ON-SITE ANALYSIS," the disclosure of which is incorporated by reference herein in its entirety. Alternately, an exemplary sample collection system comprising at least one packed bed column or capture element may be disposed in parallel to each other to selectively capture non-volatile particles in breath aerosols into each column or capture element. Each packed bed column may comprise about 200 mg of C18 resin beads. One or more suitable pumps located downstream of the capture element may be selected to provide the required flow rate through each packed bed column. Aerosol sample at an exemplary flow rate of about 20 L/min may be pulled through each column to realize a capture capacity of about 10 wt.-% (20 mg non-volatile particles/200 mg of C18 beads) in each bed. A sample capture element comprising four beds arranged in parallel to each other may provide a total flow rate of about 80 L/min through the four beds. The number of beds may be scaled-up or down to realize a desired aerosol sample flow rate through the sample capture element. For example, ten exemplary packed bed columns may be disposed in parallel to each other in a bundle or cartridge to process about 200 L/min of aerosol sample through the cartridge. The amount of C18 beads in each bed may be reduced to decrease bed length and increase the flow rate through each bed as a result of decreasing pressure drop through each bed.

As previously described, the source of aerosol samples comprising non-volatile organic aerosol particles in breath may comprise exhaled breath samples collected using a breath collection element such as a CPAP mask that is configured to receive an individual face. Aerosol particles in exhaled breath may then be pulled through a packed bed column comprising C18 beads to capture non-volatile exhaled breath particles. The exemplary sample capture element comprising a packed bed column may also be used to capture non-volatile organic particles from exhaled breath found in ambient air in a targeted area, for example, from exhaled breath in ambient air in a waiting room of a hospital or clinic, an ambulance, an operating room, an intensive care unit, and the like. Disclosed is an exemplary aerosol collection system 1400 (FIG. 10) for collecting non-volatile organic particles in ambient air present in a room, for example, in a hospital operation room. The non-volatile particles may comprise breath aerosol particles dispersed in ambient air and may comprise at least one of microbes, virus, metabolite biomarkers, lipid biomarkers, and proteomic biomarkers characteristic of a respiratory disease. System 1400 may comprise at least one sample capture element 1407 comprising a packed bed column of C18 resin beads to selectively capture the non-volatile particles when ambient air is drawn (or pulled) through the at least one element 1407 using a suitable pump 1406. Capture element 1407 may be removably disposed in enclosure 1401 using quick connect/disconnect couplings or fittings at the inlet ends 1408 and outlet ends 1409. Exemplary quick connect/disconnect couplings may comprise plug and socket fittings (latch-lock sockets, twist lock sockets, and the like) as supplied by McMaster-Carr (Cleveland, OH). Pump 1406 may be disposed inside enclosure 1401 and driven using power from power supply 1402. The couplings and mating fittings in enclosure 1401 may comprise electrical contacts to detect proper mechanical and electrical connection/contact and alert a user, for example, via a graphical user interface disposed on enclosure 1401, via an audible alarm, and the like. Alternately, pump 1406 may be disposed external to enclosure 1401 and may comprise a hospital room suction machine or pump driven by an external power source. Aerosol collection 1400 system may further comprise nebulizer element 1404 to humidify ambient air prior to entering capture elements 1407 to increase the humidity in the packed bed column to about 95% RH, which in turn may increase the particle capture efficiency of elements 1407. Alternately, nebulizer 1404 may be in the form of a sprayer or humidifier that converts water into a fine spray or mist. Water stored in container 1405 may be fed to element 1404 using pump 1403. Power supply 1402 may supply power to run pump 1403 and nebulizer 1404. An exemplary nebulizer is the Aeroneb lab micropump nebulizer and control module (Aerogen, Ireland). Exemplary pumps include diaphragm pumps and peristaltic pumps. The diameter of capture element 1407 may be between about 10 mm and about 20 mm. The internal diameter of capture element 1407 may be about 16 mm. The packed bed may comprise C18 resin beads of nominal particle diameter of between about 75 μm and about 150 μm. The bed weight in each capture element may be about 200 mg and bed length may be between about 3 mm and about 5 mm. The C18 particles may be packed between an upstream porous polymeric frit disc and a downstream porous polymeric frit disc. The pore size of the upstream and downstream discs may be about 90 μm and 35 μm, respectively. The dimensions of exemplary enclosure 1401 may be about 11 in.×11 in.×5 in. (L×H×D). As described in Example 8, greater than 99.8% of ambient air particles were captured using capture elements 1407 in system 1400 suggesting that the particle capture efficiency was at least 99% even at high gas hourly space velocities of about $2\times10^6$ per hour. Alternately, water pump 1403, pump 1406, power supply 1402, nebulizer 1404, and water container 1405 may be disposed external to enclosure 1401, for example in a separate enclosure or subsystem to reduce the size of enclosure 1401, which will render enclosure 1401 to be essentially noise free. In this exemplary aspect, enclosure 1401 may comprise the one or more sample capture elements 1407 and may be placed in the proximity of a patient in a hospital operating room.

In another exemplary aerosol collection system 1400A (FIG. 12A-D) for collecting non-volatile organic particles in ambient air present in a room, water pump 1403, water container 1405, power module 1402 and air pump 1406 (not shown) may be disposed in fluidic module 1410. Water container 1405 may have a water capacity of about 1.3 liter. Module 1410 may be a pelican case or other suitable enclosure that is portable or easily transportable. Input power may be supplied via cable 1411, which may be removably connected to wall electrical outlet (120 VAC). Module 1410 may also comprise on/off power switch 1412. Module 1410 is configured to be in fluid communication with sample collection module 1413 using suitable flexible tubings. Modules 1410 and 1413 may be disposed near each other or at a distance from each other. For example, while module 1413 may be disposed inside an operating room (OR) in a hospital, fluidic module may be disposed outside the room, or at a distance, to minimize noise generated by the pumps inside module 1410. Water in container 1405 may be transferred to reservoir 1414 using pump 1403. Reservoir 1414 may be configured to hold a predetermined volume of water, with excess water overflowing back into container 1405. Nebulizer 1404 may be disposed near the outlet of reservoir 1414. Nebulizer 1404 may be an ultrasonic mist atomizer (manufactured by DHTS, for example), powered by a 3.7-12 VDC power supply or battery. The atomizer may be energized by a power supply disposed in collection module 1413. Nebulizer 1404 may be 20 mm in diameter and may operate at about 113 kHz. Water mist generated by nebulizer 1404 may be routed through conduit 1415 into manifold 1416. Manifold 1416 may comprise a plurality of outlet ports 1417 disposed in proximity to air sample inlet ports 1418 in a second manifold 1419. Manifold 1419 may support a plurality of sample capture elements 1407 that are in fluid communication with inlet ports 1418. Details related to exemplary sample element 1407 were previously described. During sample collection, water mist is continuously generated and exit through ports 1417 to humidify ambient air drawn through ports 1418 and into capture elements 1407 using air pump 1406 (FIG. 10). Any water condensed out from the mist in collection module 1413 (condensate exiting the sample capture elements) is collected into reservoir 1420 that is suitably disposed below collection module 1413.

The packed bed in each capture element 1407 is kept moist during sample collection as ambient air is drawn into each capture element using pump 1406 at a flow rate of about 20 L/min. Pump 1403 may supply water at about 1.3 ml/min to reservoir 1414. The water flow rate may be between about 1 ml/min and about 2 ml/min. At this flow rate and using a starting water volumes of about 1.3 liter, fluidic module 1410 may supply water mist to the capture elements 1407 for about 16 h. After sample collection, the capture elements are removed from collection module 1413 and for aerosol particle extraction using suitable organic solvents. The organic solvents may comprise at least one of acetonitrile (ACN), methanol, and isopropanol (IPA), the remaining being water. The solvent may comprise between about 50 vol.-% and about 70 vol.-% acetonitrile in water to elute polar particles such as small metabolites and proteins from the bed. Another solvent may comprise between about 50 vol. % and about 70 vol. % isopropanol in water to elute non-polar particles such as lipids from the bed. The diameter of capture element 1407 may be between about 10 mm and about 20 mm. The internal diameter of capture element 1407 may be about 16 mm. The packed bed may comprise C18 resin beads of nominal particle diameter of between about 75 μm and about 150 μm. The bed weight in each capture element may be about 200 mg and bed length may be between about 3 mm and about 5 mm. The C18 particles may be packed between an upstream porous polymeric frit disc and a downstream porous polymeric frit disc. The pore size of the upstream and downstream discs may be about 90 μm and 35 μm, respectively. For capturing aerosolized virus particles, exemplary sample capture element 1001, 7001, 1301, 902, and 1407 may comprise sulfate ester-immobilized cellulose beads. Alternately, in sample collection module 1413, one or more capture elements may comprise packed beds of C18 beads and one or more capture elements 1407 may comprise packed beds of sulfate ester-immobilized cellulose beads. Alternately, in sample collection module 1413, one or more capture elements may comprise packed beds of a mixture of C18 beads a sulfate ester-immobilized cellulose beads. Exemplary sulfate beads may comprise Cellufine Sulfate beads (JKC Corp., Japan). Particle diameter may be between about 40 μm and about 130 μm. An exemplary sample capture element may comprise about 100 mg of sulfate ester-immobilized cellulose beads disposed as a packed bed column. The exemplary sample capture element may have an internal diameter of about 6.8 mm and length of about 30 mm.

In an exemplary aerosol sample collection method using systems 1400 or 1400A, sample capture elements 1407 are inserted into ports 1421 in collection module 1413. Water pump 1403 and nebulizer 1404 are energized to generate water mist to humidify ambient air drawn through ports 1418 into each sample capture element 1407. Ambient air sample is then drawn into each sample capture element 1407 using pump 1406 for a predetermined sampling time. The sampling time may be varied to cover the duration of an operation in a hospital operating room. In some instances, sampling time could be about 8 hours. Each capture element 1407 is then removed from enclosure 1401 and washed with organic solvents to elute the captured non-volatile organics from the packed bed in each element 1407. As previously described, the organic solvents may comprise at least one of acetonitrile (ACN), methanol, and isopropanol (IPA), the remaining being water. The solvent may comprise between about 50 vol.-% and about 70 vol.-% acetonitrile in water to elute polar particles such as small metabolites and proteins from the bed. Another solvent may comprise between about 50 vol.-% and about 70 vol.-% isopropanol in water to elute non-polar particles such as lipids from the bed. The bed may be first washed with ACN in water followed by IPA in water. The particles may then be concentrated using lyophilization and analyzed using a diagnostic device comprising at least one of PCR, ELISA, rt-PCR, mass spectrometer (MS), MALDI-MS, ESI-MS, and MALDI-TOFMS. Extracted particles may also be subjected to a hot digestion step to produce characteristic peptides, for example from virus particles.

Disclosed is an exemplary system 1300 (FIG. 9A) and method for capturing exhaled air aerosols by disposing exemplary sample capture element 1301 comprising a packed bed column in fluid communication with ventilator 1305. Ventilator 1305 is a life support machine and is used in intensive care units for patients who cannot breathe on their own. For example, patients with severe symptoms of COVID-19 may need the assistance of a ventilator to breathe. A tube 1306 is inserted through the patient's mouth or nose directly into the trachea. The ventilator pushes air into the lungs through this tube and forces the person to inhale. The ventilator typically forces air in for one second, pauses for about three seconds to allow the patient to exhale through the same tube, and then repeats the cycle. Inlet end 1302 of capture element 1301 is removably connected and preferably directly to the exhaled air tubing of the ventilator to minimize particle loss. Outlet end 1303 is removably connected to pump 1304 using a tubing to draw in exhaled air through the packed bed column in element 1301 at a flow rate of between about 200 ml/min and about 2.5 L/min. As in system 7000 (FIG. 7), system 1300 may comprise a trap disposed between end 1303 and pump 1304 to collect any condensate. The trap may be cooled to a temperature below ambient temperature. An optional HEPA filter and a needle valve or flow meter may be installed between the trap and the pump. $CO_2$ in exhaled breath passes through the packed bed column. To determine if exhaled breath sample volume is adequate, a $CO_2$ sensor may be disposed between the outlet end 1303 and the trap. $CO_2$ monitoring allows for an approximation of the exhaled air volume. A particle counter may also be installed between outlet end 1303 and the trap to detect the size and number for particles exiting the packed bed column, which may also be used to detect saturation of the bed and breakthrough of nonvolatile organic molecules (bacteria and virus particles) from the column bed. The capacity of the C18 beads in element 1301 to capture non-volatile organic molecules may be between about 0.05 mg (non-volatile organics)/mg beads and about 0.5 mg/mg. The capacity of C18-bonded resin beads in the column bed in exemplary capture element may be about 0.1 mg/mg. That is, a column bed having 25 mg C18 beads would be expected to be characterized by a capacity to trap or adsorb about 2.5 mg of non-volatile organic molecules. Pump 1304 may be a diaphragm pump. Data from the $CO_2$ sensor may be recorded on a non-volatile memory card such as an SD card that is commonly used in portable devices. A flow rate sensor may be installed to monitor the flow rate through the C18 packed bed column. Alternately, a flow controller may be employed to achieve a consistent flow rate, for example, a flow rate of 500 mL/min through the packed bed column. To enable exhaled breath aerosol sampling from a ventilator disposed in hospital intensive care units using exemplary capture element 1301, pump 1304 may be packaged along with a $CO_2$ sensor 1311, associated power supply 1307, system control components, and required fluidic components (tubings, quick connect/disconnect couplings at the like) into a portable system 1313 (FIG. 9B). Capture element 1301 may be disposed to be in fluid communication with system 1313 (FIG. 9B) through port 1314, which may comprise a quick connect/disconnect coupling. A portion of exhaled air leaving capture element 1301 using pump 1304 may be routed to reservoir 1312 which is fluidly connected with $CO_2$ sensor 1311. Reservoir 1312 may be a well-sealed container and is used to prevent any air leaks from the $CO_2$ sensor. System 1313 may comprise a user interface and an on-off switch to initiate and stop sampling of exhaled breath using element 1301. Additionally, components such as flow controllers, and flow restrictors 1309 may also be packaged in portable system 1313. Pump 1304 may be a diaphragm pump. Portable system 1313 may be 11 in.×7.5 in.×5.5 in. (L×D×H) and may include noise cancelling materials such as foam pads to reduce the noise level caused by the pump to less than 45 dB. After a predetermined sample collection period, sample capture element 1301 may be removed from system 1300. Element 1301 may then be autoclaved at 110° C. for about 10 minutes to disinfect element 1301 prior to extracting the captured aerosol particles. Captured nonvolatile aerosol particles may be extracted by washing (or flushing) the column with about 200 μL to about 400 μL of a solvent comprising at least one of 70% acetonitrile (ACN), about 50% to about 70% methanol, and about 50% to about 70% isopropyl alcohol (IPA). For example, 50% ACN flush may be used to elute metabolites and proteins in a first-stage flush followed by 70% IPA flush to elute lipids from the packed bed column. The organic solvent may be removed, if needed, from the packed bed column by lyophilization overnight to preserve the captured bioaerosol particles. The organic solvent may be also removed by incubating on a heating block at about 70° C. for about 30 minutes. Finally, the bed may be washed with about 0.05% TFA. The analytical methods for the analysis of metabolites, proteins, and lipids may include silver staining for protein profiling, protein assay for protein content, bottom-up proteomics and LC-MS/MS for metabolomics and lipid-omics, and MALDI-TOF mass spectrometry for molecule profiling. In an exemplary test, exhaled breath aerosol from patients infected with pneumonia were collected using capture element 1301 connected to a ventilator. During subsequent analysis, protein content measured using protein assay and molecule profiling measured using MALDI-TOF MS were found to be good indicators of pneumonia infection in patients as revealed by Pearson's correlation heatmap comprising the variables of collected total exhaled air volume, $CO_2$ content in exhaled air, protein content, MALDI-TOF total ion intensity and MALDI-TOF MS single peak (4820 m/z) intensity.

As previously described herein, the packed bed column in sample capture element 902 (FIG. 5) may comprise Hamilton PRP-C18 resin beads as supplied by Sigma Aldrich and other vendors. The resin beads may be characterized by a nominal diameter of between about 12 μm and about 20 μm. Preferably, the nominal diameter of the C18 beads is about 20 μm. The packed bed may be held in place between two porous filter plates such as frit discs. For example, a polyethylene disc having an average pore size of above 35 μm may be placed upstream of the bed, and a polyethylene disc having an average pore size of 10 μm (Boca Scientific, Dedham, MA) may be placed downstream of the bed. The 35 μm frit disc allows for higher air flow rates through the bed and minimizes undesirable pressure drop through the bed, while the smaller 10 μm frit disc traps the C18 resin beads from escaping the column. The packed bed may comprise about 25 mg of C18 resin beads. Non-volatile organic components including bacteria and virus particles in exhaled breath removably interact with the C18 functional groups on the beads and are trapped. Water, volatile organic molecules and other hydrophilic molecules pass through the bed and may be trapped in a suitable trap 904 disposed between sample capture element 902 and pump 903. Trap 904 may be cooled to below ambient temperature. Sample capture element 902 may be cooled to a temperature at or below ambient temperature. A portable laser particle counter (MetOne Instruments, Grants Pass, OR) 905 may be installed downstream of capture element 902 to measure particle counts and particle size of any particles that are not captured by capture element 902. Particle count and particle size data may be used to estimate capture efficiency of element 902 as a function of particle size. The C18 resin beads provide a surface affinity between the carbon chains on the beads and the organic molecules present on the surface of viruses and microorganisms. For example, the cell surface of bacteria, is composed of various structures of glycans; further, wax-like mycolic acids coat the surface of *M. tuberculosis*. These organic molecules are generally hydrophobic and show a significant affinity to alkyl chains of the C18 beads in the packed bed. In addition, to chemical properties, the particle size of the packed bed column and the bed length are carefully selected to provide particle capture by physical adsorption also. For capturing aerosolized virus particles and virus particles in solution, exemplary sample capture element 1001, 7001, 1301, 902, and 1407 may comprise sulfate ester-immobilized cellulose beads. Exemplary sulfate beads may comprise Cellufine Sulfate beads (JKC Corp., Japan). Particle diameter may be between about 40 μm and about 130 μm. An exemplary sample capture element may comprise about 100 mg of sulfate ester-immobilized cellulose beads disposed as a packed bed column. The exemplary sample capture element may have an internal diameter of about 6.8 mm and length of about 30 mm. As shown in Example 8, hot digestion of SARS-CoV-2 virus particles extracted using a packed bed column of sulfate ester-immobilized beads, analysis using MALDI TOFMS and processing spectra using peptide fingerprint protocols may enable peptide fingerprint matching for nucleoprotein (N) and for rapid identification of SARS-CoV-2.

The trapped aerosol particles from the packed bed column of sample capture element 902 may then be extracted using a suitable solvent for analysis. A suitable extraction system may comprise means to flush the packed bed column with a solvent and for removing the solvent comprising non-volatile organics from the packed bed. The solvent may comprise at least one of acetonitrile, methanol, acid, isopropanol, the remaining being water. The solvent may comprise between about 50 vol.-% and about 70 vol.-% acetonitrile in water. The solvent may comprise between about 50 vol. % and about 70 vol. % isopropanol in water. The solvent may comprise between about 50 vol.-% and about 70 vol.-% methanol in water. The solvent may comprise at least one of about 12.5 vol.-% acetic acid, about 5 vol.-% TFA, about 5 vol.-% formic acid and about 10 vol.-% HCl. The packed bed may be washed with water at least once prior to solvent extraction to remove water soluble inorganic contaminant particles. The collected sample may then be analyzed using a diagnostic device that comprises at least one of PCR, ELISA, rt-PCR, mass spectrometer (MS), MALDI-MS, ESI-MS, and MALDI-TOFMS. Alternately, after the collection step, the C18 beads may transferred to a capped tube comprising a suitable extraction solvent such as 70% isopropanol, shaken by hand or subjected to centrifugation to extract the captured aerosols into the solvent. In the exemplary system and methods disclosed herein, the C18 beads and/or column may be re-used after washing the beads first with organic solvents and subsequently with inorganic solvents such as water and PBS buffer solution. A diagnostic device that enables top-down proteomics such as MALDI-TOFMS may be used. In top-down proteomics, intact protein ions or large protein fragments from bacteria and viruses are subjected to gas-phase fragmentation for MS analysis.

The disclosed exemplary systems and methods may be used to establish a baseline of protein, metabolite, and lipids signatures in exhaled breath, which may then be used during to differentiate between the exhaled breath of patients with various respiratory diseases and offer a powerful diagnostic tool for disease detection based on the analysis of non-volatile aerosols in exhaled breath.

EXAMPLES

Example 1. Capture and Analysis of Aerosolized Bacteria and Virus Particles Using an Exemplary Packed Bed Column 900 and MALDI TOF-MS Capture and analysis of aerosolized *E. coli* K12 strain, Bacteriophage MS2, *Pseudomonas fluorescens* 1013, and

*Yersinia rohdei* CDC 3022-85 were examined. Aerosol particles from a water sample comprising about 20 μL of viruses or bacteria were generated using a Sono-Tek ultrasonic nozzle (Milton, NY). The nozzle was tuned to generate aerosol particles with size ranging from about 0.3 μm to about 10 μm, with median particle size of about 2 μm. The particles were directed into releasing chamber 901 (a 50 ml conical tube) having a nominal volume of about 50 ml and drawn through the packed bed column at a flow rate of about 500 ml/min for about 10 min. The packed bed column in capture element 902 comprised about 25 mg of C18 resin beads of about 20 μm in size. The beads were washed with 70% acetonitrile once and thrice with 0.05% trifluoroacetic acid. After washing, the beads were kept wet before use. For this purpose, column 902 may be capped at both ends and stored in a refrigerator to prevent drying out of the beads prior to use. The column bed was about 3 mm in length and about 7 mm in diameter. The bed volume was about 0.115 cc. At a flow rate of 500 ml/min, the gas hourly space velocity (GHSV, ratio of flow rate to bed volume) was therefore calculated to be about 260,000 per hour. Capture element 902 was removably installed near the bottom of the 50 ml conical tube. A portable laser particle counter (MetOne Instruments, Grants Pass, OR) 905 was used to measure particle sizes that ranged from about 0.3 and about 10 μm upstream and downstream of capture element 902. Trap 904 comprised of a laboratory glass reservoir cooled in ice water and was disposed downstream of element 902 to collect aerosol condensates (e.g., water vapor) passing through the column. The particle counts upstream and downstream of capture element 902 for Bacteriophage MS2 are shown in Table 1.

TABLE 1

| Particle capture efficiency of exemplary capture element 902 for aerosolized MS2 capture. | | |
|---|---|---|
| Particle size, μm | Particle count measured upstream of capture element 902 | Particle count measured downstream of element 902 |
| 0.3 | 3,921 | 12 |
| 0.5 | 4,236 | 10 |
| 1 | 15,232 | 52 |
| 2 | 17,892 | 7 |
| 5 | 1,250 | 2 |
| 10 | 365 | 0 |
| TOTAL | 42,896 | 83 |

Based on the particle counts shown in Table 1, about 99.8% of the MS2 particles were captured in the packed bed column in capture element 902 suggesting that the particle capture efficiency is at least 99% even at gas hourly space velocities of about 260,000 per hour. The packed bed column dimensions (length, diameter) and flow rate through the bed may be changed to realize gas hourly space velocities of at least 250,000 per hour. Without being bound by any particular theory, particle capture efficiency of at least 99% may be measured at gas hourly space velocities of between about 250,000 per hour and about 3,000,000 per hour. A capture efficiency of at least 99% was also measured for aerosolized *E. coli* particles. The exemplary packed bed column of length of about 3 mm therefore yielded significantly higher particle capture efficiency including particles as small as about 0.3 μm and exceeded the capture efficiency using filter substrates such as electret and Teflon filters that are between about 0.05 mm and about 0.15 mm thick. As previously described, L/Dp of the packed bed is between about 150 and 250 which prevents localized flow through the bed and exposes substantially all of the beads and surface area for trapping (chemical adsorption or physical adsorption) the bio-aerosol particles. After particle capture for about 10 min., the packed bed column was washed with about 400 μL of water thrice, after which, trapped biomaterials were eluted with 200 μL of 70% isopropanol. Samples collected during the wash and elution steps were analyzed using mass spectrometry.

MALDI-TOF mass spectra of the samples were acquired using a Shimadzu Axima CFR-plus mass spectrometer operated in the linear mode from 1000 to 15000 m/z. For direct infusion and nanoflow-LC mass spectrometry, a LTQ Orbitrap system coupled with an EASY-nLC 1000 system was used (Thermo Fisher Scientific). The flow rate for direct infusion was about 3 μL/min. For LC-MS analysis, samples were injected into an microflow C18 column (Acclaim™ PepMap™ 100, 75 μm×2 μm×25 cm, Thermo Fisher Scientific) and proteins were separated using a gradient of solvent B (99% acetonitrile with 0.1% formic acid) from 5% to 65% in 90 minutes. Ion fragmentation was conducted using the collision-induced dissociation (CID) method. To improve ion fragmentation coverage, a staged-CID approach was used, and top-down mass spectra were acquired using collision energy of 0%, 10%, 15%, 20%, 25%, 30%, and 35%, respectively. During top-down mass spectrometric data analysis, monoisotopic masses were deconvoluted using Xcalibur software (Thermo Fisher Scientific) and the fragmentation ions were examined and identified using ProSight Lite (Northwestern University).

The wash samples and elution samples (after extraction of the packed column bed) were analyzed using MALDI-TOFMS. Results showed that bacterium signatures were well represented in the elution samples suggesting that the aerosol capture and elution methods and systems disclosed herein provide for analysis of the complete or original (whole cell) biological materials. Further, the signal-to-noise between the control and elution samples was indistinguishable suggesting the capture using the packed column bed and extraction was highly effective. In fact, after a quick centrifugation on the elution samples, bacterium materials were visualized as pale pellets on the bottom of the tube, suggesting an excessively strong capture capacity of the collection system.

Most viruses have a protein shell. MS2 was used as a representative virus model to evaluate the ability of the disclosed exemplary systems and methods to capture viruses. MALDI-TOF mass spectrometric analysis showed that capsid protein, which is the historical biomarker of MS2, was observed in the elution sample. The identity of MS2 capsid protein (13729 Da, MH⁺) was confirmed using a top-down mass spectrometry approach in which high-confident statistical scores were constructed when matching the experimental fragmentation ions against in silico protein fragmentation pattern. Therefore, MALDI-TOFMS whole cell characterization and top-down protein identification were used to confirm that the disclosed aerosol capture systems and methods may be used to capture aerosolized virus particles. To further confirm the results observed using top-down mass spectrometry, direct infusion mass spectrometry and nanoflow LC mass spectrometry were used for quantitative analysis. Direct infusion mass spectrometric analysis showed that the signal intensity of referee insulin was about 3.6E+6 (FIGS. 6A-B). The signal intensity of MS2 capsid protein was about 1.1E+5 in both control sample and capture samples (sample obtained by extracting aerosols from the packed bed column), suggesting no obvious sample loss is observed using the exemplary aerosol capture system and methods and MALDI-TOFMS analysis. This observation was further confirmed using nano-flow LC mass spectrometry, a gold standard for molecule quantitative analysis. LC mass spectrometry results (FIGS. 7A-B) showed that the peak areas and ion intensity of MS2 capsid protein were substantially identical in both control and capture samples, suggesting the exemplary aerosol capture systems and methods preserved a high biochemical capture efficiency. Without being bound by any particular theory, several factors contribute to the superior capture efficiency of the disclosed aerosol capture methods even at gas hourly space velocities through the bed, including, but not limited to, the high retention capacity of C18 resin beads for aerosolized organic biomaterials such as virus and bacteria particles, the preparation of the packed bed prior to use, disposing the capture element directly to the source of aerosol particles such as aerosol releasing chamber 901, and the unique packed bed column parameters employed for capturing aerosolized particles. As previously described, the dimensions of the packed bed column provide sufficient retention time at flow rates of about 500 ml/min and ensures good contact between carbon chains on the resin beads and the organic molecules on the surface of viruses. In addition, since aerosol particles comprising viruses and microorganisms were directly exposed to the C18 beads, which "wall-losses" were minimized. Wall losses are typically present in other aerosol collection methods in which particles are deposited on the sides or walls of the device. Quantitative analysis of MS2 capsid protein demonstrated superior capture efficiency of the disclosed aerosol collection systems and methods. In addition, since no vacuum pump is used, the disclosed systems and methods may be treated as a "soft collection techniques," because they preserve the viability of whole-cell viruses, bacteria, and other microorganisms that are required for other microbiological culture studies.

Example 2. Exemplary Packed Bed Column Characteristics

The commercial use of membrane-based aerosol collection devices is plagued by clogging and pressure drop issues, which is caused by the accumulation of water droplets and other environmental particles during aerosol collection. This requires large membrane surface area, which increases costs, and high parasitic power and noisy air pumps. Aerosol capture tests were conducted using C18 beads of nominal diameter of about 10 μm and about 20 μm. The beads were packed between polymeric frit discs. The average pore size of the upstream disc and downstream disc was about 35 μm and 10 μm respectively. HPLC-grade water and E. coli vegetative cells were aerosolized into chamber 901 and pulled through an exemplary packed bed column 902 using pump 903, which is preferably a diaphragm pump. E. coli is a rod-shaped bacteria with nominal dimensions of between about 1 μm and about 2 μm in length and about 1 μm in diameter. The pump flow rate was set at 2.5 L/min and actual flow rate through the bed was measured using a flow meter (see FIG. 5). Tests were conducted using a packed bed column of C18 beads. As shown in FIG. 8A, the measured flow rate through the bed comprising about 25 mg, 20 μm C18 beads was about 750 ml/min when the bed (about 3 mm in length) was exposed to HPLC-grade water aerosols, and about 600 ml/min when the bed was exposed to E. coli aerosols over 30 min of capture time. This result suggests that the 25 mg bed of about 20 μm, C18 beads was not saturated during these tests indicating that the amount of the beads in the bed may be reduced. Alternately, the capture time may be increased using a 25 mg bed. In contrast, when the bed comprised 10 µm C18 beads, flow rate decreased from about 200 ml/min to about 50 ml/min in about 30 min when the bed was exposed to HPLC-grade water aerosols. Further, flow rate decreased from about 100 ml/min to about 3 ml/min when the bed was exposed to *E. coli* aerosols indicating significant pressure drop through the bed comprising 10 µm beads. These results suggest that C18 beads in the packed bed column in capture element 902 of particle size of at least about 20 µm is preferred.

Further, the impact on flow rate reduction due to increasing pressure drop across the bed was examined by varying the quantity of C18 beads in the packed bed column, and pore size of the polymeric frit disc disposed at the inlet end of the bed. The pump flow rate was set at 2.5 L/min and actual flow rate through the bed was measured using a flow meter. The amount of C18 beads of nominal diameter of about 20 µm was increased from about 25 mg to about 40 mg in the packed bed column. The average pore size of the upstream disc and downstream disc was about 35 µm and 10 µm respectively. Increasing the bed amount from about 25 mg to about 40 mg increased the bed length from about 3 mm to about 5 mm. In each case, flow rate through the bed was monitored after exposing the bed to aerosolized HPLC-grade water aerosols. The results (FIG. 8B) show that increasing the amount of C18 beads in the bed from about 25 mg to about 40 mg resulted in a decrease in the flow rate from about 700 ml/min to about 150 ml/min after 30 min of collection time. Further, in a separate set of tests, the pore size of the inlet polymeric frit disc was changed from 35 µm to about 10 µm. During exposure to aerosols of *E. coli* (vegetative cells), the flow rate decreased from about 600 ml/min to about 250 ml/min during the 30 min. collection time. (FIG. 8C).

Example 3. Capture and Analysis of Exhaled Air Aerosols of Patients Diagnosed with COVID-19 Using an Exemplary Packed Bed Column Connected to a Ventilator Exemplary system 1300 (FIG. 9A) was evaluated in a hospital intensive care unit (ICU) dedicated for treating patients diagnosed with the COVID-19 disease. The flow rate through the packed bed column comprising about 25 mg of C18 beads (20 µm nominal diameter) in sample capture element 1301 was set at 500 ml/min. Before installing in system 1300, the capture element was washed with 70% acetonitrile once and then thrice with 0.05% TFA. The capture elements were stored at 4° C. before use to prevent drying out of the C18 beads in the packed bed. Exhaled breath aerosol was then collected for about 4 h from each patient at a flow rate of 500 ml/min. After the collection period, the packed bed columns were removed from the collection system. The columns were washed with about 200 µL to about 400 µL of 70% ACN or 70% IPA. The organic solvent was removed from the packed bed column by lyophilization overnight. The organic solvent may also be removed by placing element 1301 on a heating block at about 70° C. for about 30 minutes. The captured aerosol particles were the extracted or resolved using between about 40 µL and 100 µL of 0.05% TFA. The samples were then analyzed using SDS-PAGE electrophoresis and silver staining, MALDI-TOFMS (whole cell top-down proteomics), and bottom-up proteomics.

About 5 µl of total collected sample was used for SDS-PAGE electrophoresis, which was conducted using a Criterion Tris-HCl Gel system (Bio-Rad Laboratories, Hercules, CA). After SDS-PAGE electrophoresis, the SDS-PAGE gel was prepared with a silver staining kit (Thermo Fisher Scientific) for the visualization of protein bands. Bovine serum albumin was used as an internal positive control. Protein bands were observed in all 3 patient samples. Based on the BSA control sample, the protein content in 3 samples was estimated to be at least 100 ng.

For whole cell MALDI-TOFMS analysis, 0.2 µL of analytes was mixed with 0.2 µL of α-Cyano-4-hydroxycinnamic acid MALDI matrix (CHCA) prepared in 70% ACN. The mixture was deposited onto a MALDI sample cap and mass spectra were collected using an exemplary MALDI-TOF mass spectrometry system disclosed in commonly owned Pat. Appl. No. PCT/US20/48042 titled "SYSTEMS AND METHODS OF RAPID AND AUTONOMOUS DETECTION OF AEROSOL PARTICLES," which is incorporated by reference herein in its entirety. MALDI-TOF spectra were collected from the samples of patient #3 and #4. Mass peaks were observed in both samples. The peak patterns generated from MALDI-TOF MS were examined using pattern recognition algorithms for detection and classification.

For bottom-up proteomics, 5 µl of each sample was used. About 50 µl of 50 mM ammonia bicarbonate (pH 8.5) was added to each sample. Protein reduction was conducted by adding dithiothreitol to a final concentration of 5 mM and incubating for 30 min at 37° C. After reduction, protein alkylation was followed by adding iodoacetamide to a final concentration of 15 mM and incubating for 1 h at room temperature. Trypsin (Thermo Fisher Scientific) was used for an overnight protein digestion. After digestion, peptides were cleaned up using C18-packed tips (Glygen, Columbia, MD). The peptide samples in 20 µl of 0.1% formic acid were then prepared for mass spectrometry analysis, including MALDI-TOF mass spectrometry. Samples were processed using an EASY-nLC 1000 system (Thermo Fisher Scientific) coupled to a LTQ Quadrupole-Orbitrap mass spectrometer (Thermo Fisher Scientific). For tandem mass spectrometry analysis, peptides were loaded into an Acclaim PepMap 100 C18 trap column (0.2 mm×20 mm, Thermo Fisher Scientific) with a flow rate of 5 µl/min and separated on an EASY-Spray HPLC Column (75 µm×150 mm, Thermo Fisher Scientific). HPLC gradient was conducted using 5%-55% of the mobile phase (75% acetonitrile and 0.1% formic acid) with a flow rate of 300 nl/min for 60 min. Mass spectrometry data collection was conducted in the data dependent acquisition mode. Precursor scanning resolution was set to 30,000 and product ion scanning resolution 15,000. Product ion fragmentation was achieved using high energy collision-induced disassociation with 30% total energy. The bottom-up proteomics raw data files were processed with MaxQuant Andromeda software (maxquant.org) against the "human" and "SARS-COV-2" protein database (uniprot.org) following the standard recommendations and instructions. Human protein database included 20,395 reviewed proteins and SARS-COV-2 protein database included 13 reviewed proteins. Liquid chromatography profiles and peptide fingerprints generated from the digested peptides were identified using LC-MS and MALDI-TOF MS in all three patient samples. In total, 222 proteins were identified in all three patient samples. Most proteins were found to originate from human blood, indicating active interaction between lungs and blood. As shown in Table 2, typical lung proteins and SARS-COV-2 protein were identified.

TABLE 2

Proteins identified from exhaled air aerosols collected from patients diagnosed with COVID-19.

| Protein identification list | Mol. weight [kDa] |
|---|---|
| sp\|P0DTD1\|R1AB__SARS2 Replicase polyprotein 1ab OS = Severe acute respiratory syndrome coronavirus 2 OX = 2697049 GN = rep PE = 1 SV = 1 | 794.05 |
| sp\|Q9HC84\|MUC5B__HUMAN Mucin-5B OS = *Homo sapiens* OX = 9606 GN = MUC5B PE = 1 SV = 3 | 596.33 |
| sp\|P02671\|FIBA__HUMAN Fibrinogen alpha chain OS = *Homo sapiens* OX = 9606 GN = FGA PE = 1 SV = 2 | 94.972 |
| sp\|P02768\|ALBU__HUMAN Serum albumin OS = *Homo sapiens* OX = 9606 GN = ALB PE = 1 SV = 2; | 69.366 |
| sp\|P02675\|FIBB__HUMAN Fibrinogen beta chain OS = *Homo sapiens* OX = 9606 GN = FGB PE = 1 SV = 2 | 55.928 |
| sp\|Q8TDL5\|BPIB1__HUMAN BPI fold-containing family B member 1 OS = *Homo sapiens* OX = 9606 GN = BPIFB1 PE = 1 SV = 1 | 52.441 |
| sp\|P63261\|ACTG__HUMAN Actin, cytoplasmic 2 OS = *Homo sapiens* OX = 9606 GN = ACTG1 PE = 1 SV = 1; sp\|P60709\|ACTB__HUMAN Actin, cytoplasmic 1 OS = *Homo sapiens* OX = 9606 GN = ACTB PE = 1 SV = 1 | 41.792 |
| sp\|P35247\|SFTPD__HUMAN Pulmonary surfactant-associated protein D OS = *Homo sapiens* OX = 9606 GN = SFTPD PE = 1 SV = 3 | 37.728 |
| sp\|P02647\|APOA1__HUMAN Apolipoprotein A-I OS = *Homo sapiens* OX = 9606 GN = APOA1 PE = 1 SV = 1 | 30.777 |
| sp\|Q8IWL2\|SFTA1__HUMAN Pulmonary surfactant-associated protein A1 OS = *Homo sapiens* OX = 9606 GN = SFTPA1 PE = 1 SV = 2; sp\|Q8IWL1\|SFPA2__HUMAN Pulmonary surfactant-associated protein A2 OS = *Homo sapiens* OX = 9606 GN = SFTPA2 PE = 1 SV = 1 | 26.242 |
| sp\|P68871\|HBB__HUMAN Hemoglobin subunit beta OS = *Homo sapiens* OX = 9606 GN = HBB PE = 1 SV = 2 | 15.998 |
| sp\|P69905\|HBA__HUMAN Hemoglobin subunit alpha OS = *Homo sapiens* OX = 9606 GN = HBA1 PE = 1 SV = 2 | 15.257 |
| sp\|Q99879\|H2B1M__HUMAN Histone H2B type 1-M OS = *Homo sapiens* OX = 9606 GN = H2BC14 PE = 1 SV = 3; sp\|Q99877\|H2B1N__HUMAN Histone H2B type 1-N OS = *Homo sapiens* OX = 9606 GN = H2BC15 PE = 1 SV = 3; sp\|Q93079\|H2B1H__HUMAN Histone H2B type 1-H OS = *Homo sapiens* OX = 9606 GN = HIST1H2BH PE | 13.989 |
| sp\|P0DJI8\|SAA1__HUMAN Serum amyloid A-1 protein OS = *Homo sapiens* OX = 9606 GN = SAA1 PE = 1 SV = 1 | 13.532 |
| sp\|P06702\|S10A9__HUMAN Protein S100-A9 OS = *Homo sapiens* OX = 9606 GN = S100A9 PE = 1 SV = 1 | 13.242 |
| sp\|P02656\|APOC3__HUMAN Apolipoprotein C-III OS = *Homo sapiens* OX = 9606 GN = APOC3 PE = 1 SV = 1 | 10.852 |
| sp\|P11684\|UTER__HUMAN Uteroglobin OS = *Homo sapiens* OX = 9606 GN = SCGB1A1 PE = 1 SV = 1 | 9.9937 |

Example 4. Capture of Ambient Air Aerosol Particles Using an Exemplary Collection System 1400

Capture of particles in ambient air were examined using exemplary system 1400 comprising four capture elements 1407. Each element 1407 comprised about 200 mg of C18 beads of nominal diameter between about 75 µm and 150 µm packed between two porous frit discs in a polymeric tubing of internal diameter of about 16 mm. The packed bed length was about 3 mm yielding a bed volume of about 0.6 cc. Air was pulled through each column at a flow rate of about 20 L/min using pump 1406. The packed bed was wetted with water prior to sample capture. Particle size and count was measured using a Met One Instruments particle counter. The particle counts upstream and downstream of capture element 1407 are shown in Table 3.

TABLE 3

Particle capture efficiency using exemplary collection system 1400.

| Particle size, µm | Particle count in ambient air | Particle counts measured downstream of system 1400 at time = 0 | Particle counts measured downstream of system 1400 at time = 60 min |
|---|---|---|---|
| 0.3 | 101,000 | 116 | 125 |
| 0.5 | 7,000 | 10 | 0 |
| 0.7 | 651 | 52 | 0 |
| 1 | 294 | 7 | 0 |
| 2 | 163 | 2 | 0 |
| 5 | 10 | 0 | 0 |
| TOTAL | 109,118 | 116 | 125 |

Based on the particle counts shown in Table 3, greater than 99.8% of ambient air particles were captured using capture elements 1407 in system 1400 suggesting that the particle capture efficiency is at least 99% even at gas hourly space velocities of about $2 \times 10^6$ per hour. When used for capturing non-volatile organic aerosols such as protein, lipid and metabolite biomarkers and whole pathogens, the capture capacity of the bed may be about 10 wt.-%.

Example 5. Analysis of Exhaled Breath Collected from Healthy Human Subjects to Establish a Baseline of Metabolites and Lipids in Exhaled Breath In exemplary system 7000, the column in element 7001 comprised about 35 mg of C18 beads of nominal diameter between about 55 μm and 105 μm. The packed bed of C18 beads was disposed between an upstream porous frit having a pore size of about 90 μm and a downstream frit having a pore size of about 35 μm. The diameter of element 7001 was about 6 mm and bed length was about 3 mm. At a bed volume of about 0.09 cc and flow rate pulled through the bed of about 3 L/min, gas hourly space velocity (GHSV) through the bed was high at about $2 \times 10^6$ per hour, which allows for flexibility in either increasing the flow rate through the bed further or decreasing bed volume. As discussed below, even at this high space velocity, efficient capture of nonvolatile organics particles such as metabolites and lipids were demonstrated. Three capture elements (columns) 7001 were used for capturing exhaled breath aerosols from each human subject sequentially in time: 10 minutes for the first column, thereafter, 10 minutes for the second column, and thereafter, 10 minutes for the third column. The first column was washed using ACN to elute metabolites. The second column was washed with 300 μL of 70% IPA to elute lipids. The third column was used as a control and only collected HEPA-filtered air. During sample collection, a $CO_2$ sensor was used to sense and record $CO_2$ level in the exhaled breath of each individual. The $CO_2$ sensor was located between exit of column and the pump.

The eluted metabolite and lipid samples were lyophilized overnight. The dried samples were prepared in solutions for LC-MS/MS analysis. Total ion chromatography (TIC) in LC-MS analysis was used for peak alignment and intensity normalization. Metabolite and lipid identification was based on accurate mass measurement and MS/MS spectral matching using an open-source software MS-DIAL (PRIMe platform by RIKEN Metabolomics, Japan). To eliminate minor peaks, data was filtered (data filtration) as follows: low ion intensity peaks were ignored, and in addition, if peaks were only identified in only one subject, these peak was treated as an artifact and ignored. The ion peaks in the sample from the third column (HEPA filtered air) were used as a baseline filter and these peaks were excluded from all breath samples. The individual $CO_2$ concentration measured during sample collection from each subject was used for ion intensity normalization of individual breath samples; that is, ion intensity values were divided by individual $CO_2$ concentration. Individual $CO_2$ concentrations (ppm) were between a minimum of about 6850 ppm and maximum of about 12799 ppm during sample collection using the first column (sample capture element). During sample collection using the second column, $CO_2$ concentrations fell between 4925 ppm and 16453 ppm. The final human breath sample database constructed from this study included molecule identifications, retention time, full mass, and ion fragmentation information (MS/MS).

Using data science software RStudio, principal component analysis (PCA) and partial least squares-discriminant analysis (PLS-DA) were employed to visualize breath and blank samples. As shown in FIG. 11A, a distinct segregation between the breath samples and HEPA-filtered air (blank) samples for both metabolites and lipids in human breath was observed. A similar segregation is also expected during analysis of breath samples from healthy human subjects and from human subjects infected from a respiratory disease. Also, as shown in FIG. 11, about 1804 metabolites and 1150 lipids were identified in the breath samples and not in the HEPA-filtered air (blank) samples. Relative standard deviation (RSD, 0-300%) showed that lipids were characterized by a greater number of identifications that were below 100% RSD which suggests that standard deviation from the mean for lipids related to breath collection samples from the 14 subjects is quite small, and gives greater confidence that lipid biomarkers from exhaled breath aerosols collected and eluted using the exemplary systems and methods may be used to discriminate between healthy and patients infected with respiratory diseases. Finally, ion intensities from each individual captured samples (for the 14 subjects) were normalized using their $CO_2$ concentrations measured during sample collection. As shown in FIG. 11C, this normalization protocol highlights certain variations in ion intensities for both lipid and metabolite biomarkers (top 5 ion intensities in each case) for certain subjects and may be used to better understand metabolite and lipid biomarker characteristics of healthy individuals, which can then be subsequently used during interpretation of data collected from infected patients.

Example 6. Capture and Bottom-Up Proteomics of Ambient Air Aerosol Particles Using an Exemplary Collection System 1400A Capture of particles in ambient air was examined using exemplary system 1400A comprising four capture elements 1407. Each element 1407 comprised about 200 mg of C18 beads of nominal diameter between about 75 μm and 150 μm packed between two porous frit discs in a polymeric tubing of internal diameter of about 16 mm. The packed bed length was about 3 mm yielding a bed volume of about 0.6 cc. Air was pulled through each column at a flow rate of about 20 L/min using pump 1406 and was humified prior to entering the sample capture elements. Four samples were collected, namely, (1) from a single-occupancy (one person) office with 8 h of air sampling, (2) from a cafeteria with 8 people and 2 h of air sampling, (3) and two samples from a low-traffic operating room in a hospital with no occupancy and 7 h of air sampling. After sample collection, the aerosol particles in each packed bed column were eluted using 2 mL 10-80% organic solvent followed by an overnight lyophilization to remove the organic solvent. For each sample, the residual proteins were evaluated with protein silver staining and bottom-up proteomics.

60 proteins were identified from the office air sampling sample, 72 proteins were identified from the cafeteria air sample, 84 proteins were identified from the low-traffic operating room (OR) air sample #1, and 38 proteins were identified from the low-traffic operating room air sample #2 (FIG. 13A). Typical proteins were identified and comprised keratins in all four samples (Table 4), which was evidence of proteins from human activity. The level of keratin-9 was evaluated and showed that the office sample collected from a room with a single person occupancy contained the most keratin-9 (FIG. 13B).

TABLE 4

Protein list showing protein tissue origins in the four
air samples collected using exemplary system 1400A.

| Protein ID | Proteins | Origin |
|---|---|---|
| | Office | |
| P81605 | Dermcidin | Skin, Upper and lower airways |
| P35527 | Keratin, type I cytoskeletal 9 | Skin |
| P35247 | Pulmonary surfactant-associated protein D | Lower airways |
| Q9NZT1 | Calmodulin-like protein 5 | Skin |
| | Cafeteria | |
| Q9UMD9 | Collagen alpha-1(XVII) chain | Skin |
| P04264 | Keratin, type II cytoskeletal 1 | Skin |
| Q9BSE2 | Transmembrane protein 79 | Skin |
| P01040 | Cystatin-A | Lower airways |
| P35527 | Keratin, type I cytoskeletal 9 | Skin |
| | Low-traffic OR 01 | |
| P28289 | Tropomodulin-1 | Muscle |
| P04264 | Keratin, type II cytoskeletal 1 | Skin |
| P63261 | Actin, gamma-enteric smooth muscle | Upper airways |
| P35527 | Keratin, type I cyloskeletal 9 | Skin |
| Q7Z5P9 | Mucin-19 | Upper and lower airways |
| | Low-traffic OR 02 | |
| P35527 | Keratin, type I cytoskeletal 9 | Skin |

Example 7. Aerosolized Protein Capture Using
Exemplary Sample Capture Element with C18
Packed Bed Column and a Commercial Button
Sampler The exemplary sample capture element comprised of a packed bed column of C18 beads of nominal diameter between about 45 μm and 120 μm. The amount of C18 beads in the column was about 200 mg and bed length was about 3 mm. The length and diameter (ID) of the capture element was about 60 mm and about 15.9 mm respectively. The Button Sampler (SKC Ltd, United Kingdom) comprised a filter sampler (25 mm filters with pore size greater than 1 μm) with a porous curved-surface inlet designed to improve the collection characteristics of inhalable dust (100 μm aerodynamic diameter), including bioaerosols for total microbial count.

Protein solution comprising BSA protein in artificial saliva (NCZ-APS-0012) background solution with a BSA concentration of about 2 mg/ml was aerosolized using a Dynamic Concentration Aerosol Generator at the Applied Physics Laboratory at Johns Hopkins University. In the case of the exemplary sample capture element, a mechanical pump was used to draw the aerosol through the packed bed column at about 10 L/min. After sample collection, the C18 beads packed bed column was eluted with 2 mL of 70% CAN and the organic solvent was removed by an overnight lyophilization. The sample was suspended in 50 μL of water and used for SDS-PAGE electrophoresis, blue staining, and bottom-up proteomics.

FIG. 14 shows protein blue staining of samples collected using the exemplary C18 packed bed column and the button sampler. As can be seen, the protein capture efficiency of the C18 exemplary packed bed column was significantly better than that obtained using the button sampler. Further, in the case of silver staining, BSA protein bands (about 66 kDa) were not seen in samples collected with the button sampler. In contrast, BSA protein bands were seen in all samples collected with the exemplary C18 packed bed column. Besides intact BSA protein, its dimmer form (about 140 kDa) and trimmer form (about 200 kDa) were seen in all samples collected with the C18 packed bed column.

Example 8. Capture of SARS-CoV-2 Virus Using
Sulfate Ester Functional Groups and Analysis SARS-CoV-2 South African strain was grown using the cell line Vero E6 TMPR332. 0.3 mL of the virus was combined with PBS buffer solution to make a final volume of 4.7 mL. The growth media was decanted from the tissue culture vessel and gently washed thrice with 20 mL of PBS. 5 mL of diluted virus was pipetted to a vessel and incubated f at 37° C. for 15 minutes. 20 mL of un-supplemented media was added to each vessel and incubated for 2 days until CPE of about 80% was achieved. At the time of harvest, the CPE was 90%. TCID50 was concentrated to 2.32 e+7 (calculated by Reed & Muench method). In a purification step, the virus was ultra-centrifuged at 100,000 g for 60 min., the supernatant was decanted, and the pellet was resuspended in 1 mL of water. The virus was then heat inactivated at 70° C. for 30 min.

The sample capture element comprised sulfate ester-immobilized cellulose beads (Cellufine® Sulfate). The packed bed column comprised beads of diameter of between about 40 mm and about 130 mm. The packed bed column (30 mm length×6.8 mm ID) comprised about 100 mg of beads. The column was washed once with 1 mL of washing solution (0.2 M NaCl in 1×PBS). 900 μL of the SAR-CoV-2 virus sample was prepared in 100 μL of 10×PBS to make a final solution of 1×PBS solution. The entire sample solution with the virus was loaded into the column using a syringe and pushed through the column. The sample exiting the column was collected and pushed through the column 5 more times to maximize virus capture in the bed. To completely remove non-binding proteins, 2 mL of 0.2 M NaCl in 1×PBS washing solution was pushed through the column three times. Subsequently, air was pushed through the column to ensure that washing solution was left in the column. The captured virus particles were then eluted using 900 μL of 1.5 M NaCl in 1×PBS elution solution.

The eluted sample was split into two samples and each sample was subjected to hot acid digestion. Prior to this step, the eluted sample was filtered in a centrifuge. 200 μL of eluted virus was combined with 250 μL of HPLC water and loaded into a 3 k (3 kDa MWCO) filter column. The sample was spun in a microcentrifuge at 14,000 g for 25 minutes. The 3 k column was topped off with 450 μL of HPLC water and spun again. This process was repeated thrice. The column was flipped upside-down in a new hold tube and centrifuged for 10 minutes at 10,000 g. This sample was used for hot acid digestion. The sample produced from the 3 k filtration was topped with about 50.5 μL of water to make a final sample volume of 87.5 μL. 12.5 μL of acetic acid was added to make a 12.5% acid solution (100 μL in total). The samples were subjected to hot acid digestion at about 140° C. for about 15 min.

The sample was then analyzed using MALDI-TOF mass spectrometry. CHCA matrix was prepared in 70% acetonitrile at a concentration of about 9 mg/mL. About 1 μl of the hot acid samples was deposited onto a MALDI plate. Once the sample was partially dried, about 1 μl of the CHCA solution was deposited on top and mixed by pipetting up and down. The samples were analyzed using a commercial Bruker Daltonics microflex LRF MALDI-TOF mass spectrometer. MALDI-TOF mass spectra were obtained in the positive linear mode and an average of 600 profiles were collected in a mass range of 700-21,000 m/z for all spectra. The online program MASCOT Peptide Mass Fingerprint (Matrix Science, Boston, MA) was used to identify peptide mass fingerprints. Mass peaks with S/N>10 were extracted into "Mass values" for analysis. "SwissProt" protein database was used, and "All entries" was selected for taxonomy. Enzyme was defined as "Formic_acid," and different missed cleavage numbers, 0-9, were allowed. Peptide tolerance was set to 0.5 Da and monoisotopic type was selected.

Figures 15A, 15B, 15C, 15D:
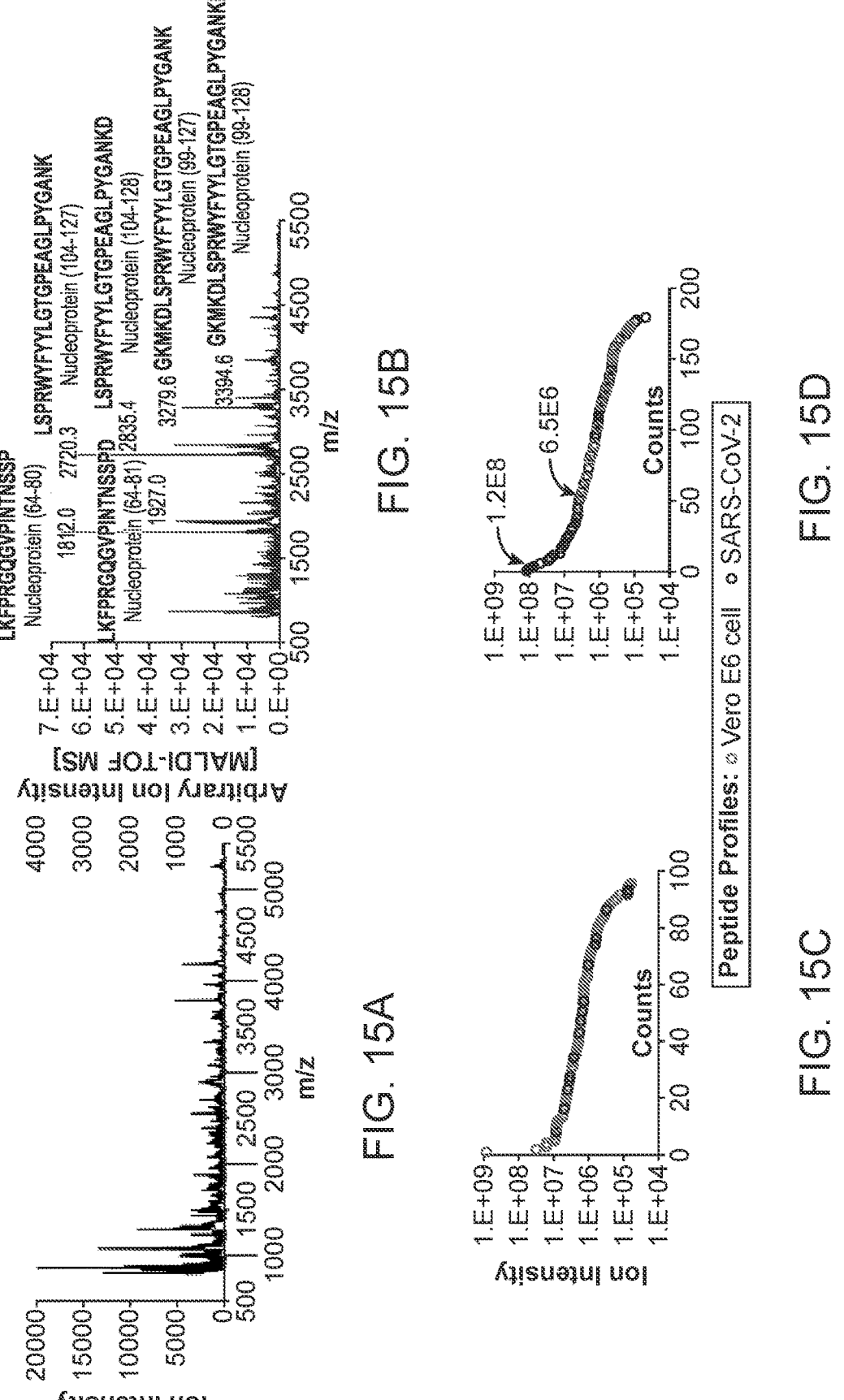

FIG. 15A-B show MALDI TOF mass spectra of hot acid digested peptides from virus samples extracted from the sulfate ester packed bed column showed a more distinct profile compared to spectra of samples that were not treated with the sulfate ester packed bed column. Bottom-up proteomics was used for the peptide identification and showed that peptides of Vero E6 cell proteins were most abundant in the samples that were not treated with the sulfate ester packed bed column (FIG. 15C). In contrast, samples extracted from the sulfate ester packed bed column showed that peptides of SARS-CoV-2 proteins were most abundant (FIG. 15D-E). Viral peptides were also characterized by significantly higher ion intensities (FIG. 15D) in the samples extracted from the sulfate ester packed bed column. These results demonstrate that sulfate ester immobilized cellulose beads may be used for capture of aerosolized virus particles. Further, bottom-up proteomics showed that the identified peptides correspond to N protein characteristic of SARS-CoV-2. Using peptide identification information from bottom-up proteomics, six mass peaks were identified in MALDI-TOF MS spectra (FIG. 15B) characteristic of SARS-CoV-2. The typical mass shifting signature in hot acid-assisted hydrolysis, +115.1, was observed in these peak assignment.

Since most of the peptides identified after the enrichment correspond to N protein, MALDI-TOF MS mass peaks from samples extracted from the exemplary capture element may be used for the identification of N protein using peptide mass fingerprinting and following SARS-CoV-2 detection. 37 mass peaks with the signal-to-noise ratio greater than 10 were selected and processed with MASCOT Peptide Mass Fingerprint program. Since hot acid-assisted protein hydrolysis causes missed cleavage, the effect of allowed missed cleavage on the identification scores was evaluated. The results showed that N protein can be confidently identified using MALDI-TOF mass spectral profiles when the missed cleavage was larger than 0 (FIG. 15E). Among the identification results, three allowed missed cleavage sites resulted in the best score and the score did not vary significantly when larger missed cleavage numbers were used. The results showed that the combination of rapid MALDI-TOF MS and peptide mass fingerprinting can be used for the detection of SARS-CoV-2.

The exemplary sulfate ester packed bed column and sample extraction, processing and analysis methods may be used to capture and identify other virus particles also. The peptides identified using MALDI-TOF MS and by Mascot database searching can also be used for distinguishing different strains of the SARS-CoV-2 virus. For example, Eta/B.1.525. strain has a SD>Y transition at amino acid positions 2 and 3 from the natural variant from reference database UniProtKB—PODTC9 (NCAP_SARS2). Alpha/B.1.1.7. has a D>L transition at the amino acid position 3 from the natural variant. Eta/B.1.525. has a A>G transition at the amino acid position 12 from the nature variant. Omicron/B.1.1.529. has a P>L transition at the amino acid position 13 from the nature variant. The amino acid positions 31-33 are missing in Omicron/B.1.1.529. from the nature variant. Delta/B.1.617.2. has a D>G transition at the amino acid position 63 from the nature variant. Gamma/P.1. has a P>R transition at the amino acid position 80 from the nature variant. Delta/B.1.617.2 and Kappa/B.1.617.1. have a D>Y transition at the amino acid position 377 from the nature variant.

The Abstract is provided to comply with 37 C.F.R. § 1.72(b), to allow the reader to determine quickly from a cursory inspection the nature and gist of the technical disclosure. It should not be used to interpret or limit the scope or meaning of the claims.

Although the present disclosure has been described in connection with the preferred form of practicing it, those of ordinary skill in the art will understand that many modifications can be made thereto without departing from the spirit of the present disclosure. Accordingly, it is not intended that the scope of the disclosure in any way be limited by the above description.

It should also be understood that a variety of changes may be made without departing from the essence of the disclosure. Such changes are also implicitly included in the description. They still fall within the scope of this disclosure. It should be understood that this disclosure is intended to yield a patent covering numerous aspects of the disclosure both independently and as an overall system and in both method and apparatus modes.

Further, each of the various elements of the disclosure and claims may also be achieved in a variety of manners. This disclosure should be understood to encompass each such variation, be it a variation of an implementation of any apparatus implementation, a method or process implementation, or even merely a variation of any element of these.

Particularly, it should be understood that the words for each element may be expressed by equivalent apparatus terms or method terms—even if only the function or result is the same. Such equivalent, broader, or even more generic terms should be considered to be encompassed in the description of each element or action. Such terms can be substituted where desired to make explicit the implicitly broad coverage to which this disclosure is entitled. It should be understood that all actions may be expressed as a means for taking that action or as an element which causes that action. Similarly, each physical element disclosed should be understood to encompass a disclosure of the action which that physical element facilitates.

In addition, as to each term used it should be understood that unless its utilization in this application is inconsistent with such interpretation, common dictionary definitions should be understood as incorporated for each term and all definitions, alternative terms, and synonyms such as contained in at least one of a standard technical dictionary recognized by artisans and the Random House Webster's Unabridged Dictionary, latest edition are hereby incorporated by reference.

Further, the use of the transitional phrase "comprising" is used to maintain the "open-end" claims herein, according to traditional claim interpretation. Thus, unless the context requires otherwise, it should be understood that variations such as "comprises" or "comprising," are intended to imply the inclusion of a stated element or step or group of elements or steps, but not the exclusion of any other element or step or group of elements or steps. Such terms should be interpreted in their most expansive forms so as to afford the applicant the broadest coverage legally permissible.

REFERENCES

1. Fennelly K. P., Martyny J. W., Fulton K. E., Orme I. M., Cave D. M., et al. (2004) Cough-generated aerosols of

*Mycobacterium tuberculosis*: a new method to study infectiousness. Am J Respir Crit Care Med 169: 604-609.
2. Hunt, J., "Exhaled breath condensate: An evolving tool for noninvasive evaluation of lung disease," J. Allergy Clin. Immunol. 2002; 110:28-34.
3. Benjamin Patterson, Carl Morrow, Vinayak Singh, Atica Moosa, Melitta Gqada, Jeremy Woodward, Valerie Mizrahi, Wayne Bryden, Charles Call, Shwetak Patel, Digby Warner, Robin Wood, "Detection of *Mycobacterium tuberculosis* bacilli in bio-aerosols from untreated TB patients," Gates Open Research 2018, 1:11.
4. Wood R., Morrow C., Barry C. E., III, Bryden W. A., Call C. J., Hickey A. J., et al.: Real-Time Investigation of Tuberculosis Transmission: Developing the Respiratory Aerosol Sampling Chamber (RASC). PLoS One. 2016; 11(1): e0146658.
5. Rachel C. Wood, Angelique K. Luabeya, Kris M. Weigel, Alicia K. Wilbur, Lisa Jones-Engel, Mark Hatherill, and Gerard A. Cangelosi, "Detection of *Mycobacterium tuberculosis* DNA on the oral mucosa of tuberculosis patients," Sci. Rep. 5, 8668 (2015).

What is claimed is:

1. An exhaled breath collection system for monitoring a patient infected with a respiratory disease and breathing through an exhaled air tubing of a ventilator, the system comprising:
   one or more sample capture elements configured to selectively capture aerosol particles in exhaled air produced by the patient, the one or more sample capture elements comprising:
      an inlet end removably connected directly to a capnography port disposed on a first end of the exhaled air tubing of the ventilator to minimize aerosol particle loss; and
      a packed bed column in each of the one or more sample capture elements, wherein the packed bed column is kept in a wet state prior to use by washing with one or more organic solvents and water, and wherein a second end of the exhaled air tubing is configured to be inserted through the patient's mouth or nose directly into the trachea; and
   a subsystem disposed in fluid communication with an outlet end of the one or more sample capture elements, the subsystem comprising:
      a pump disposed downstream of the outlet end of the one or more sample capture elements and configured to draw exhaled air including aerosol particles into the one or more sample capture elements;
      a power supply; and
      and a controller, wherein the subsystem is configured to control the operation of the one or more sample capture elements, and wherein a sub-micron particle capture efficiency associated with the exhaled breath collection system is at least 99%.

2. The system of claim 1, wherein the subsystem further comprises at least one of a $CO_2$ sensor and a particle counter disposed between the sample capture element and the pump, wherein the particle counter is configured to detect saturation of the bed and breakthrough of aerosolized particles from the packed bed column in each of the one or more sample capture elements.

3. The system of claim 1, wherein the subsystem is disposed in a portable enclosure, wherein the portable enclosure is configured to reduce the noise level caused by the pump to less than about 45 dB.

4. The system of claim 2, further comprising a trap disposed between the one or more sample capture elements and the pump and configured to trap exhaled breath condensate (EBC) comprising at least one of water vapor, volatile organic components, and non-volatile organic components that pass through the packed bed column in each of the one or more sample capture elements.

5. The system of claim 1, wherein the packed bed column in each of the one or more sample capture elements comprises solid particles comprising one or more of resins, cellulose, silica, agarose, or hydrated $Fe_3O_4$ nanoparticles.

6. The system of claim 1, wherein the packed bed column in each of the one or more sample capture elements comprises one or more of resin beads having C18 functional groups on the surface, cellulose beads having sulfate ester functional groups on the surface, or mixtures thereof.

7. The system of claim 6, wherein the resin beads and cellulose beads have a nominal diameter of at least about 20 μm.

8. The system of claim 6, wherein the resin beads and cellulose beads have a nominal diameter of between about 40 μm and about 150 μm.

9. The system of claim 1, wherein a nominal flow rate drawn through the packed bed column in each of the one or more sample capture elements using the pump is between about 200 ml/min and about 3 L/min.

10. A system for monitoring a patient infected with a respiratory disease and breathing using a ventilator, the system comprising:
   the exhaled breath collection system of claim 1;
   a sample extraction system to extract the aerosol particles from the packed bed column in each of the one or more sample capture elements into one or more liquid samples; and
   an analytical device to analyze the aerosol particles in the one or more liquid samples.

11. The system of claim 10, wherein the extraction system comprises means to flush the packed bed column in each of the one or more sample capture elements with at least one solvent and collect the solvent comprising aerosol particles from the packed bed.

12. The system of claim 11, wherein the at least one solvent comprises at least one of acetonitrile (ACN), methanol, trifluoro acetic acid (TFA), and isopropanol (IPA), the remaining being water.

13. The system of claim 11, wherein the one or more solvents comprises between about 50 vol.-% and about 70 vol.-% acetonitrile in water, between about 50 vol.-% and about 70 vol.-% isopropanol in water, and between about 0.05 vol.-% TFA in water.

14. The system of claim 10, wherein the analytical device comprises at least one of PCR, ELISA, rt-PCR, mass spectrometer (MS), MALDI-MS, ESI-MS, and MALDI-TOFMS, and LC-MS/MS.

15. The system of claim 1, wherein the aerosol particles in exhaled air produced by the ventilator comprises at least one of microbes, viruses, metabolite biomarkers, lipid biomarkers, and proteomic biomarkers characteristic of the respiratory disease.

* * * * *